US011714096B2

(12) United States Patent
Smith et al.

(10) Patent No.: US 11,714,096 B2
(45) Date of Patent: Aug. 1, 2023

(54) CAROUSEL FOR MODULAR BIOLOGIC PRODUCTION UNITS

(71) Applicant: OCTANE BIOTECH INC., Kingston (CA)

(72) Inventors: Timothy Smith, Kingston (CA); Ian Grant, Kingston (CA); Guy Oram, Kingston (CA); Chase McRobie, Kingston (CA); Raelyn Daniels, Kingston (CA); Taylor Plant, Kingston (CA)

(73) Assignee: OCTANE BIOTECH INC., Kingston (CA)

( * ) Notice: Subject to any disclaimer, the term of this patent is extended or adjusted under 35 U.S.C. 154(b) by 643 days.

(21) Appl. No.: 16/719,306

(22) Filed: Dec. 18, 2019

(65) Prior Publication Data

US 2020/0200781 A1 Jun. 25, 2020

Related U.S. Application Data

(60) Provisional application No. 62/783,529, filed on Dec. 21, 2018.

(51) Int. Cl.
*G01N 35/02* (2006.01)
*C12M 3/00* (2006.01)
*G01N 35/04* (2006.01)

(52) U.S. Cl.
CPC ........... *G01N 35/025* (2013.01); *C12M 23/48* (2013.01); *G01N 2035/0441* (2013.01); *G01N 2035/0484* (2013.01); *G01N 2035/0494* (2013.01)

(58) Field of Classification Search
CPC ......... G01N 35/025; G01N 2035/0441; G01N 2035/0484; G01N 2035/0494;
(Continued)

(56) References Cited

U.S. PATENT DOCUMENTS 4,642,120 A 2/1987 Nevo et al.
4,939,151 A 7/1990 Bacehowski et al.
(Continued)

FOREIGN PATENT DOCUMENTS

AU 2002/324169 A1 3/2003
DE 4021123 A1 4/1991
(Continued)

OTHER PUBLICATIONS

Andris et al., "Naive T Cells are Resistant to Anergy Induction by Anti-CD3 Antibodies," The Journal of Immunology (2004) 173(5):3201-3208.
(Continued)

*Primary Examiner* — Jill A Warden
*Assistant Examiner* — John McGuirk
(74) *Attorney, Agent, or Firm* — Medler Ferro Woodhouse & Mills PLLC

(57) ABSTRACT

An automated carousel and system configured for translationally moving a plurality of biological production units in unison along a vertical frame while maintaining a precise alignment of each of the biological production units relative to gravity, and simultaneously providing independent dynamic adjustment of the axial orientation of each of the plurality of biological production units relative to gravity. The automated carousel may be adapted for use with a variety of biological production units supporting cell culture and/or tissue engineering systems in various clinical and laboratory settings and provides for ergonomic use thereof.

15 Claims, 11 Drawing Sheets

(58) Field of Classification Search
CPC .......... G01N 2035/0417; C12M 23/48; C12M 23/50; C12M 23/44; C12M 41/48; B65G 1/12; B65G 1/133; B65G 47/00
See application file for complete search history.

(56) References Cited

U.S. PATENT DOCUMENTS

| | | |
|---|---|---|
| 5,041,138 A | 8/1991 | Vacanti et al. |
| 5,081,036 A | 1/1992 | Familletti |
| 5,240,854 A | 8/1993 | Berry et al. |
| 5,246,699 A | 9/1993 | Debre et al. |
| 5,424,209 A | 6/1995 | Kearney |
| 5,478,479 A | 12/1995 | Herrig |
| 5,549,134 A | 8/1996 | Browne et al. |
| 5,688,687 A | 11/1997 | Palsson et al. |
| 5,728,581 A | 3/1998 | Schwartz et al. |
| 5,786,207 A | 7/1998 | Katz et al. |
| 5,792,603 A | 8/1998 | Dunkelman et al. |
| 5,827,729 A | 10/1998 | Naughton et al. |
| 5,842,477 A | 12/1998 | Naughton et al. |
| 5,846,828 A | 12/1998 | Peterson et al. |
| 5,882,929 A | 3/1999 | Fofonoff et al. |
| 5,891,455 A | 4/1999 | Sittinger et al. |
| 5,902,741 A | 5/1999 | Purchio et al. |
| 5,906,934 A | 5/1999 | Grande et al. |
| 5,922,604 A | 7/1999 | Stapleton et al. |
| 5,928,936 A | 7/1999 | Ingram |
| 5,985,653 A | 11/1999 | Armstrong et al. |
| 5,989,913 A | 11/1999 | Anderson et al. |
| 5,994,129 A | 11/1999 | Armstrong et al. |
| 6,048,721 A | 4/2000 | Armstrong et al. |
| 6,048,722 A | 4/2000 | Farb et al. |
| 6,060,306 A | 5/2000 | Flatt et al. |
| 6,096,532 A | 8/2000 | Armstrong et al. |
| 6,121,042 A | 9/2000 | Peterson et al. |
| 6,123,655 A | 9/2000 | Fell |
| 6,197,575 B1 | 3/2001 | Griffith et al. |
| 6,214,574 B1 | 4/2001 | Kopf |
| 6,228,635 B1 | 5/2001 | Armstrong et al. |
| 6,238,908 B1 | 5/2001 | Armstrong et al. |
| 6,297,046 B1 | 10/2001 | Smith et al. |
| 6,323,146 B1 | 11/2001 | Pugh et al. |
| 6,402,941 B1 | 6/2002 | Lucido et al. |
| 7,348,175 B2 | 5/2008 | Vilendrer et al. |
| 7,906,323 B2 | 3/2011 | Cannon et al. |
| 8,492,140 B2 | 7/2013 | Smith et al. |
| 8,727,132 B2 | 5/2014 | Miltenyi et al. |
| 9,499,780 B2 | 11/2016 | Smith et al. |
| 9,534,195 B2 | 1/2017 | Smith et al. |
| 9,629,877 B2 | 4/2017 | Cooper et al. |
| 9,701,932 B2 | 7/2017 | Smith et al. |
| 9,783,768 B2 | 10/2017 | Larcher et al. |
| 10,131,876 B2 | 11/2018 | Kaiser et al. |
| 10,253,316 B2 | 4/2019 | Masquelier et al. |
| 10,273,300 B2 | 4/2019 | Bedoya et al. |
| 11,208,626 B2 | 12/2021 | Mason et al. |
| 2001/0021529 A1 | 9/2001 | Takagi |
| 2001/0043918 A1 | 11/2001 | Masini et al. |
| 2002/0009797 A1 | 1/2002 | Wolf et al. |
| 2002/0009803 A1 | 1/2002 | Vajta |
| 2002/0025547 A1 | 2/2002 | Rao |
| 2002/0037580 A1 | 3/2002 | Schoeb |
| 2002/0146816 A1 | 10/2002 | Vellinger et al. |
| 2002/0155487 A1 | 10/2002 | Greenberger et al. |
| 2002/0179525 A1 | 12/2002 | Shaffer et al. |
| 2003/0032071 A1 | 2/2003 | Wang et al. |
| 2003/0040104 A1 | 2/2003 | Barbera-Guillem |
| 2003/0054335 A1 | 3/2003 | Taya et al. |
| 2003/0159946 A1 | 8/2003 | Eden et al. |
| 2003/0215935 A1 | 11/2003 | Coon |
| 2004/0048364 A1 | 3/2004 | Trosch |
| 2005/0019904 A1 | 1/2005 | Zarur |
| 2005/0064465 A1 | 3/2005 | Dettloff et al. |
| 2005/0130297 A1 | 6/2005 | Sarem et al. |
| 2005/0186671 A1 | 8/2005 | Cannon et al. |
| 2007/0172396 A1* | 7/2007 | Neeper ............ G01N 35/0099 422/400 |
| 2009/0003981 A1* | 1/2009 | Miller ................ G01N 35/04 62/440 |
| 2014/0166601 A1* | 6/2014 | Peters ............... B41F 13/0016 211/60.1 |
| 2015/0344844 A1 | 12/2015 | Better et al. |
| 2016/0122782 A1 | 5/2016 | Crisman et al. |
| 2017/0037369 A1 | 2/2017 | Ramsborg et al. |
| 2017/0051252 A1 | 2/2017 | Morgan et al. |
| 2017/0254826 A1 | 9/2017 | Eberle |
| 2019/0004077 A1* | 1/2019 | van Mierlo ........... B65G 17/32 |
| 2019/0169572 A1 | 6/2019 | Shi et al. |
| 2019/0211294 A1 | 7/2019 | Karnieli |

FOREIGN PATENT DOCUMENTS

| | | |
|---|---|---|
| EP | 0248675 A1 | 12/1987 |
| GB | 1356794 A | 6/1974 |
| JP | 2-119772 A | 5/1990 |
| JP | 2-174848 A | 7/1990 |
| JP | 3-500847 A | 2/1991 |
| JP | 5-503418 A | 6/1993 |
| JP | 6-54678 A | 3/1994 |
| JP | 6-261736 A | 9/1994 |
| JP | 7-501206 A | 2/1995 |
| JP | H08-56646 A | 3/1996 |
| JP | H11-507229 A | 6/1999 |
| JP | 2001-275659 A | 10/2001 |
| JP | 2001-517428 A | 10/2001 |
| JP | 2002-500004 A | 1/2002 |
| KR | 200243145 Y1 | 9/2001 |
| WO | 91/05849 A1 | 5/1991 |
| WO | 93/03142 A1 | 2/1993 |
| WO | 1997/12960 A2 | 4/1997 |
| WO | 99/33951 A1 | 7/1999 |
| WO | 99/47922 A2 | 9/1999 |
| WO | 2000/046349 A1 | 8/2000 |
| WO | 01/02030 A2 | 1/2001 |
| WO | 2001/000783 A2 | 1/2001 |
| WO | 2002/028996 A1 | 4/2002 |
| WO | 02/088295 A1 | 11/2002 |
| WO | 03/022985 A2 | 3/2003 |
| WO | 03/087292 A2 | 10/2003 |
| WO | 2003/085101 A1 | 10/2003 |
| WO | 2015/162211 A1 | 10/2015 |
| WO | 2016/069993 A1 | 5/2016 |
| WO | 2016/118780 A1 | 7/2016 |
| WO | 2016/168275 A1 | 10/2016 |
| WO | 2017/068425 A1 | 4/2017 |
| WO | 2018/015561 A1 | 1/2018 |
| WO | 2018/136566 A1 | 7/2018 |

OTHER PUBLICATIONS

Atkuri et al., "Culturing at atmospheric oxygen levels impacts lymphocyte function," PNAS (2005) 102(10):3756-3759.

Austyn et al., "T cell activation by anti-CD3 antibodies: function of Fc receptors on B cell blasts, but not resting B cells, and CD18 on the responding T cells." European Journal of Immunology (1987) 17(9):1329-1335.

Avgoustiniatos et al., "Commercially Available Gas-Permeable Cell Culture Bags May Not Prevent Anoxia in Cultured or Shipped Islets," Transplant Proc. (2008) 40(2):395-400.

Baroja et al., "The anti-T cell monoclonal antibody 9.3 (Anti-CD28) provides a helper signal and bypasses the need for accessory cells in T Cell activation with immobilized anti-CD3 and mitogens," Cellular Immunology (1989) 120(1):205-217.

Berdeja et al., "First-in-human multicenter study of bb2121 anti-BCMA CAR T-cell therapy for relapsed/refractory multiple myeloma: Updated results," Journal of Clinical Oncology (2017) 35(15):3010.

Bohnenkamp et al., "Bioprocess development for the cultivation of human T-lymphocytes in a clincal scale," Cytotechnology (2002) 38:135-145.

Carpenter et al., "Non-Fc Receptor-Binding Humanized Anti-CD3 Antibodies Induce Apoptosis of Activated Human T Cells," The Journal of Immunology (2000) 165(11):6208-6213.

(56) References Cited

OTHER PUBLICATIONS

Ceuppens et al., "T cell unresponsiveness to the mitogenic activity of OKT3 antibody results from a deficiency of monocyte Fc gamma receptors for murine IgG2a inability to cross-link the T3-Ti complex," The Journal of Immunology (1985) 135(6):3882-3886.
Chai et al., "Immobilized anti-CD3 mAb induces anergy in murine naive and memory CD4+ T cells in vitro.," Int Immunol. (1997) 9(7):935-944.
Charron et al., "Monocyte:T cell interaction regulates human T cell activation through a CD28/CD46 crosstalk," Immunol Cell Biol. (2015) 93(9):796-803.
Church et al., "Tumor-specific CD4+T cells maintain effector and memory tumor-specific CD8+T cells," European Journal of Immunology (2014) 44:69-79.
Clavreul et al., "Interelationship between CD3 and CD28 pathways in a murine T cell thymoma," Molecular Immunology (2000) 37(10):571-577.
Dudley et al., "Generation of Tumor-Infiltrating Lymphocyte Cultures for Use in Adoptive Transfer Therapy for Melanoma Patients," J Immunother. (2003) 26(4):332-342.
Fathman et al., "Molecular mechanisms of CD4+T-cell anergy," Nature Reviews Immunology (2007) 7:599-609.
FDA, Available online at: https://www.fda.gov/downloads/AdvisoryCommittees/CommitteesMeetingMaterials/Drugs/OncologicDrugsAdvisoryCommittee/UCM566166.pdf.
FDA, Regenerative Medicine Advanced Therapy Designation. (2017). Available at: https://www.fda.gov/BiologicsBloodVaccines/CellularGeneTherapyProducts/ucm537670.htm. (Accessed: Aug. 8, 2017).
FDA, Sepax Cell Separation System and single use kits. (2011). Available at: https://www.fda.gov/downloads/BiologicsBloodVaccines/BloodBloodProducts/ApprovedProducts/SubstantiallyEquivalent510kDeviceInformation/UCM278385.pdf. (Accessed: Nov. 8, 2017).
Feldmann et al., "Novel humanized and highly efficient bispecific antibodies mediate killing of prostate stem cell antigen-expressing tumor cells by CD8+ and CD4+ T cells," J Immunol. (2012) 189(6):3249-3259.
Fleischer et al., "Differential expression and function of CD80 (B7-1) and CD86 (B7-2) on human peripheral blood monocytes," Immunology (1996) 89(4):592-598.
Gottschalk et al., The hype, hope and reality of personalization. The Medicine Maker (2015) p. 38-41.
Greenwald et al., "The B7 Family Revised," Annual Review of Immunology (2005) 23:515-548.
Grishagin, Ivan V., "Automatic cell counting with ImageJ," Analytical Biochemistry (2015) 473:63-65.
Hammill et al., "Designed ankyrin repeat proteins are effective targeting elements for chimeric antigen receptors," Journal for ImmunoTherapy of Cancer (2015) 3(55):1-11.
Harding et al., "CD28-mediated signalling co-stimulates murine T cells and prevents induction of anergy in T-cell clones," Nature (1992) 356:607-609.
Hasegawa et al., "In vitro Stimulation of CD8 and CD4 T Cells by Dendritic Cells Loaded with a Complex of Cholesterol-Bearing Hydrophobized Pullulan and NY-ESO-1 Protein: Identification of a New HLA-DR15-Binding CD4 T-Cell Epitope," Clinical Cancer Research (2006) 12(6):1921-1927.
Hollyman et al., "Manufacturing validation of biologically functional T cells targeted to CD19 antigen for autologous adoptive cell therapy," J Immunother. (2009) 32(2):169-180.
Ju et al., "A functional anti-human 4-1BB ligand monoclonal antibody that enhances proliferation of monocytes by reverse signaling of 4-1BBL," Hybrid Hybridomics (2003) 22(5):333-338.
Kaiser et al., "Towards a commercial process for the manufacture of genetically modified T cells for therapy," Cancer Gene Therapy (2015) 22:72-78.
Kalos et al., "T Cells with Chimeric Antigen Receptors Have Potent Antitumor Effects and Can Establish Memory in Patients with Advanced Leukemia," Sci Transl Med. (2011) 3(95):1-21.
Kebriaei et al., "Phase I trials using *Sleeping Beauty* to generate CD19-specificCAR T cells," The Journal of Clinical Investigation (2016) 126(9):3363-3376.
Kochenderfer et al., "Chemotherapy-Refractory Diffuse Large B-Cell Lymphoma and Indolent B-Cell Malignancies Can Be Effectively Treated With Autologous T Cells Expressing an Anti-CD19 Chimeric Antigen Receptor," Journal of Clinical Oncology (2016 33(6):540-549.
Lafferty et al., "A new analysis of allogeneic interactions," Aust J Exp Biol Med Sci. (1975) 53(1):27-42.
Laux et al., "Response Differences between Human CD4+ and CD8+ T-Cells during CD28 Costimulation: Implications for Immune Cell-Based Therapies and Studies Related to the Expansion of Double-Positive T-Cells during Aging," Clinical Immunology (2000) 96(3):187-197.
Ledbetter et al., "CD28 Ligation in T-cell Activation: Evidence for Two Signal Transduction Pathways," Blood (1990) 75(7):1531-1539.
Levine et al., "Global Manufacturing of Car T Cell Therapy," Molecular: Therapy: Methods & Clinical Development (2017) 4:92-101.
Li et al., "Comparison of anti-CD3 and anti-CD28-coated beads with soluble anti-CD3 for expanding human T cells: Differing impact on CD8 T cell phenotype and responsiveness to restimulation," Journal of Translational Medicine (2010) 8(104):1-15.
Lock et al., "Automated Manufacturing of Potent CD20-Directed Chimeric Antigen Receptor T Cells for Clinical Use," Human Gene Therapy (2017) 28(10):914-925.
Locke et al., "Abstract CT019: Primary results from ZUMA-1: a pivotal trial axicabtagene ciloleucel (axicel; KTE-C19) in patients with refractory aggressive non-Hodgkin lymphoma (NHL)," Cancer Research (2017) 77(13).
Locke et al., "Phase 1 Results of ZUMA-1: A Multicenter Study of KTE-C19 Anti-CD19 CAR T Cell Therapy in Refractory Aggressive Lymphoma," Molecular Therapy (2017) 25(1):285-295.
Lu et al., "A Rapid Cell Expansion Process for Production of Engineered Autologous CAR-T Cell Therapies," Human Gene Therapy Methods (2016) 27(6):209-218.
Lu et al., "Automated dynamic fed-batch process and media optimization for high productivity cell culture process development," (2013) 110(1):191-205.
Lu et al., "Treatment of Patients with Metastatic Cancer Using a Major Histocompatibility Complex Class II-Restricted T-Cell Receptor Targeting the Cancer Germline Antigen MAGE-A3," Journal of Clinical Oncology (2017) 35(29):3322-3329.
Mock et al., "Automated manufacturing of chimeric antigen receptor T cells for adoptive immunotherapy using CliniMACS Prodigy," Cytotherapy (2016) 18(8):1002-1011.
Morrissey et al., "End-to-End Cell Therapy Automation: An Immunotherapy Case Study," BioPharm International (2017) 2:10-18.
Nilsson et al., "Optimal Blood Mononuclear Cell Isolation Procedures for Gamma Interferon Enzyme-Linked Immunospot Testing of Healthy Swedish and Tanzanian Subjects," Clinical and Vaccine Immunology (2008) 15(4):585-589.
Nociari et al., "A novel one-step, highly sensitive fluorometric assay to evaluate cell-mediated cytotoxicity," Journal of Immunological Methods (1998) 213(2):157-167.
Odeleye et al., "On the fluid dynamics of a laboratory scale single-use stirred bioreactor," Chemical Engineering Science (2014) 111(100):299-312.
Reusch et al., "A tetravalent bispecific TandAb (CD19/CD3), AFM11, efficiently recruits T cells for the potent lysis of CD19+ tumor cells," MAbs (2015) 7(3):584-604.
Riddell et al., "Adoptive Therapy with Chimeric Antigen Receptor Modified T Cells of Defined Subset Composition," Cancer J (2014) 20(2):141-144.
Riddell et al., "The use of anti-CD3 and anti-CD28 monoclonal antibodies to clone and expand human antigen-specific T cells," Journal of Immunological Methods (1990) 128(2):189-201.
Romagnani, S, "Type 1 T helper and type 2 T helper cells: functions, regulation and role in protection and disease," Int J Clin Lab Res (1991) 21(2):152-158.

(56) References Cited

OTHER PUBLICATIONS

Schwartz, RH, "A cell culture model for T lymphocyte clonal anergy," Science (1990) 248(4961):1349-1356.
Schwartz, RH, "T cell anergy," Annu Rev Immunol. (2003) 21:305-334.
Tangying et al., "A Rapid Cell Expansion Process for Production of Engineering Autologous CAR-T Cell Therapies," Human Gene Therapy Methods (2016) 27(6):209-218.
Tax et al., "Polymorphism in mitogenic effect of IgG1 monoclonal antibodies against T3 antigen on human T cells," Nature (1983) 304(5925):445:447.
Trainor et al., "Rethinking clinical delivery of adult stem cell therapies," Nature Biotechnology (2014) 32:729-735.
Trickett et al., "T cell stimulation and expansion using anti-CD3/CD28 beads," Journal of Immunological Methods (2003) 275(1-2):251-255.
Tuefferd et al., "HER2 Status in Ovarian Carcinomas: A Multicenter GINECO Study of 320 Patients," PLoS ONE (2007) 11:e1138.
Turtle et al., "CD19 CAR—T cells of defined $CD4^+$ :$CD8^+$ composition in adult B cell ALL patients," The Journal of Clinical Investigation (2016) 126(6):2123-2138.
Vanseggelen et al., "Chimeric antigen receptor—engineered T cells as oncolytic virus carriers," Molecular Therapy—Oncolytics (2015) 150014.
Verwilghen et al., "Differences in the stimulating capacity of immobilized anti-CD3 monoclonal antibodies: variable dependence on interleukin-1 as a helper signal for T-cell activation," Immunology (1991) 72:269-276.
Wang et al., "Clinical manufacturing of CAR T cells: foundation of a promising therapy" Mol. Ther.—Oncolytics (2016) 3:16015.
Wang et al., "Manufacture of tumor- and virus-specific T lymphocytes for adoptive cell therapies," Cancer Gene Ther. (2015) 22(2):85-94.
Wauwe et al., "OKT3: a monoclonal anti-human T lymphocyte antibody with potent mitogenic properties," The Journal of Immunology (1980) 124(6):2708-2713.
Wegener, C, "Cell Washing with the LOVO Cell Processing System," BioProcess International (2014) p. 78.
Weiss et al., "T cell activation: differences in the signals required for IL 2 production by nonactivated and activated T cells," J Immunol (1985) 135(6):3669-3673.
Wolf et al., "Induction of anergy in resting human T lymphocytes by immobilized anti-CD3 antibodies," European Journal of Immunology (1994) 24(6):1410-1417.
Yan et al., "HER2 expression status in diverse cancers: review of results from 37,992 patients," Cancer Metastasis Rev (2015) 34:157-164.
Zhu et al., "CD137 stimulation delivers an antigen-independent growth signal for T lymphocytes with memory phenotype," Immunobiology (2007) 109(11):4882-4889.
Shi et al., Performance of Mammalian Cell Culture Bioreactor with a New Impeller Design, Biotechnology and Bioengineering, Jun. 20, 1992, pp. 260-270, vol. 40, John Wiley & Sons, Inc.
Declaration from Mark Selker, Submitted in *Lonza Walkersville, Inc. v. Adva Biotechnology LTD.*, United States District Court for the District of Maryland, Case No. 8:20-cv-03099-PX, Jan. 5, 2022.
Declaration from James C. Leung, Submitted in *Lonza Walkersville, Inc. v. Adva Biotechnology LTD.*, United States District Court for the District of Maryland, Case No. 8:20-cv-03099-PX, Jan. 7, 2022.
Konstantin B. Konstantinov "Monitoring and Control of the Physiological State of Cell Cultures" Biotechnology and Bioengineering, vol. 52, pp. 271-289 (1996) (Year: 1996).
Farndale "Pulsed Electromagnetic Fields Promote Collagen Production in Bone Marrow Fibroblasts via Athermal Mechanisms" Calcif Tissue Int (1985) 37:178-182.

Aitken-Christie et al., Automation in Plant tissue culture—general introduction and overview, in Automation and Environmental Control in Plant Tissue Culture 757 (J. Aitken-Christie, T. Kozai & M. Lila Smith eds., 1995).
Apel et al., Integrated Clinical Scale Manufacturing System for Cellular Products Derived by Magnetic Cell Separation, Centrifugation and Cell Culture, Chemie Ingenieur Technik (2013).
Armstrong et al., Clinical Systems for the Production of Cells and Tissues for Human Therapy, in Novel Therapeutics From Modern Biotechnology 221 (D.L. Oxender et al. eds., 1999).
Blaeschke et al., Induction of A Central Memory and Stem Cell Memory Phenotype in Functionally Active CD4+ and CD8+ CAR T Cells Produced in an Automated Good Manufacturing Practice System for the Treatment of CD19+ Acute Lymphoblastic Leukemia, Cancer Immunology, Immunotherapy vol. 67, pp. 1053-1066 (2018), published Mar. 31, 2018.
Bousso, T-cell activation by dendritic cells in the lymph node: lessons from the movies, 8 Nature Reviews Immunology 675 (2008) ("Bousso 2008").
Basic and Clinical Immunology: Antigen Presentation, T Cell Activation and Deactivation, CLEVELANDCLINICCME, found at https://www.youtube.com/watch?v=EfYpkA4AmFo (2017), last visited Dec. 6, 2020 ("Cleveland Clinic video").
Kempner et al., A Review of Cell Culture Automation, 7 Journal of the Association for Laboratory Automation 56 (2002) ("Kempner 2002").
Koller et al., Clinical-scale human umbilical cord blood cell expansion in a novel automated perfusion culture system, Bone Marrow Transplantation (1998) ("Koller 1998").
Koller et al., Large-Scale Expansion of Human Stem and Progenitor Cells from Bone Marrow Mononuclear Cells in Continuous Perfusion Cultures, Blood (1993) ("Koller 1993A").
Koller et al., Tissue Engineering: Reconstitution of Human Hematopoiesis Ex Vivo, Biotechnology and Bioengineering (1993) ("Koller 1993B").
Kostov et al., Low-Cost Microbioreactor for High-Throughput Bioprocessing, 72 Biotechnology and Bioengineering, Feb. 5, 2001 ("Kostov 2001").
Krug et al., A GMP-compliant protocol to expand and transfect cancer patient T cells with mRNA encoding a tumorspecific chimeric antigen receptor, Cancer Immunol Immunotherapy (2014) ("Krug 2014").
Morse, Technology evaluation: Stem-cell therapy, Aastrom Biosciences Inc., Current Opinion in Molecule Fherapeutics (1999) ("Morse 1999").
Oh et al., Frequent Harvesting from Perfused Bone Marrow Cultures Results in Increased Overall Cell and Progenitor Fxpansion, Biotechnology and Bioengineering (1994).
Priesner et al., Automated Enrichment, Transduction, and Expansion of Clinical- Scale CD62L+ T Cells for Manufacturing of Gene Therapy Medicinal Products, 27 Human Gene Therapy 10, 860-869 (2016).
Rosazza et al., Gene Electrotransfer: A Mechanistic Perspective, Current Gene Therapy (2016) ("Rosazza 2016").
Stiff et al., Autologous transplantation of ex vivo expanded bone marrow cells grown from small aliquots after high-Tose chemotherapy for breast cancer, Blood (2000) ("Stiff 2000").
Zhang et al., Characterization of clinical grade CD19 chimeric antigen receptor T cells produced using automated CliniMACS Prodigy system, Drug Design, Development and Therapy (2018) ("Zhang 2018").
Zhu et al., Closed-system manufacturing of CD19 and dual-targeted CD20/19 chimeric antigen receptor T cells using the CliniMACS Prodigy device at an academic medical center, CytoTherapy (2018).

\* cited by examiner

| Measurement | Letter | Female 5% | Female 95% | Male 5% | Male 95% |
|---|---|---|---|---|---|
| Standing Eye Height | C | 57.3" | 65.3" | 60.8" | 68.6" |
| Standing Forward Reach | D | 29.7" | 34.1" | 31.9" | 37.3" |
| Sitting Knee Height | G | 17.9" | 21.5" | 19.3" | 23.4" |

CAROUSEL FOR MODULAR BIOLOGIC PRODUCTION UNITS

CROSS-REFERENCE TO RELATED APPLICATIONS

The present application claims benefit of U.S. Provisional Application No. 62/783,529, filed Dec. 21, 2018, the disclosure of which is incorporated by reference herein in its entirety.

FIELD

This invention relates to an upright carousel that provides translational movement of multiple biologic production units along a defined vertical path while maintaining each individual unit stable relative to gravity and further provides for separate dynamic axial rotation of each independent unit. The carousel is automated and adaptable for use with a variety of modular biologic production units designed for cell culture and/or tissue culture systems in various clinical and laboratory settings. The carousel and related systems and methods allow ergonomic and practical access to each of the biologic production units.

BACKGROUND

Existing engineered robotic systems for automated cell culture and tissue engineering processes are complex, require significant laboratory space for operation, and represent a substantial capital equipment investment.

Equipment design is frequently recognized as a key component in the success of GMP (Good Manufacturing Practice) biologics manufacturing, but is not always implemented with full appreciation of the processing implications. In the case of mammalian cell culture, there are recognized issues and risks that develop when transitioning to a large automated scale of operation. The developing demand for cell culture production capacity in the biopharmaceutical industry has led to a progressive increase in the scale of automated operation.

There is a growing demand for patient-specific treatments, such as for autologous cell therapy. Autologous cell therapy requires complex multiple concurrent processing events placing considerably more demands with respect to automation. Automated production units can only service one patient at any given production cycle. Scaling for large parallel processing for large numbers of patients generates the need for developing space-efficient organization and access to multiple production units within a production facility.

Accordingly, it is desirable to develop ways to achieve maximized cell and/or tissue production in existing production facility confines. Further, it is desirable to develop ways to achieve maximized cell and/or tissue production in existing production facility confines that does not detrimentally affect the integrity of the cell and tissue culture systems. It is also desired to improve ergonomics for users of automated cell and tissue engineering systems.

The discussion of the background herein is included to explain the context of the inventions described herein. This is not to be taken as an admission that any of the material referred to was published, known, or part of the common general knowledge as of the priority date of any of the claims.

SUMMARY

Herein described is a more economical and space efficient manner to operate several biological production units in a production facility where floor space is in demand, while providing a practical and ergonomic access to the cell and/or tissue culture systems within each of the biological production units.

Set forth is an upright automated carousel configured to support several biological production units that can be translationally moved along the vertical path of the carousel in unison and stopped to a user selected position for access to any one of the biological production units. During this translational movement each individual unit remains stable relative to gravity, that is, remains properly orientated horizontal to gravity. Concurrently, the automated carousel further provides for individual dynamic adjustment of axial rotation of any one or all of the units. Proper orientation of each of the units relative to gravity is maintained during active translation of the units and when the carousel is stationary. Similarly, the individual dynamic adjustment of the axial orientation of any one or all of the units can be actuated during active translational movement of the units or when the carousel is stationary Advantageously, the operation of the automated carousel for user positioning does not negatively affect the cell and/or tissue culture/engineering processes that are supported within any one of the biological production units.

Advantageously, the automated carousel is configured so that each of the biological production units supported on the carousel is independently operable and customized with respect to the cell and/or tissue culture/engineering processes that are supported within any one of the biological production units.

Advantageously, the biological production units supported on the carousel are so linked that the operational resources required for each of the biological production units are optionally one central means for ease of use. Surprisingly, the linkage to the central operational resources is operationally maintained during translational movement of the biological units along the vertical curved path of the carousel and during any individual adjustment of axial rotation of any one of the units. This is particularly advantageous for being able to provide multiple biological production units on a single carousel each with customized cell and/or tissue culture/engineering processes, yet optionally all share the same central operational resources and also share the same translational movement ability for user positioning and separate ability for independent axial rotation.

The automated carousel of the invention is advantageously configured to utilize vertical space for the distribution, operation and uniform translational movement of multiple biological production units arranged in a close spatial relationship along its curved vertical path. Translational movement is in a vertical plane and follows the curved shape of the carousel. Translational movement may be up to about 180 degrees clockwise or counterclockwise, of varying speeds and is user controlled. The translational movement is designed to be precise and in controlled increments such that an operator (no matter what height) can position any one of the biological units to a position for ergonomic access whether in a standing or a sitting position. The carousel is configured with a safety stop mechanism to stop movement at any time as desired or required. The axial rotation of any one individual biological production unit may also be clockwise or counterclockwise to provide a rocking motion or for agitation.

Attachment of the biological production units to the carousel is reversible such that each unit can be inspected, removed, replaced or repositioned to a different position on the carousel or to a different carousel. In an aspect, the biological production units are attached in a cantilevered orientation to allow easier access by a user and to maintain the efficient use of floor space.

It is contemplated that different types of biological production units may be mounted to one carousel so long as the basic size, weight and independent functioning capabilities are comparable to other units mounted on the carousel in order not to negatively affect the overall balance of the carousel, the uniform bi-directional translational movement along the carousel frame, the gravitational orientation of the biological production units mounted thereon, or the ability to independently dynamically adjust the bi-directional axial orientation relative to gravity of any one of the units. Further, each of the biological production units mounted on the carousel may support a different cell culture and/or tissue culture system therein customized for a specific need or a specific patient.

The automated carousel may be provided as a system disposed vertically within a vertical housing for central operation and central provision of operational resources to each of the independently controlled biological production units that function to support a cell and/or tissue culture system therein. The vertical housing serves as a support frame and attachment structure for the carousel to maintain an upright positioning of the carousel and for its operation. The vertical housing is configured to readily permit reversible attachment of the biological production units, their proper translational movement along the carousel shape, and for user access. The vertical housing has a supporting base and retractable wheels for ease of relocation. The vertical housing is configured for ease of assembly and disassembly, for centrally storing required resources and for user safety.

User access, service access and space efficiency is improved when supporting multiple biological production units on an automated carousel of the invention. Furthermore, the carousel of the invention can provide increased expandability, by taking full advantage of the height of a biological production facility. Several carousels can be arranged and used in series. Therefore numerous biological production units can be run in a production facility in a space efficient yet operator accessible manner.

The carousel is used in conjunction with one or more controllers, controller communications interface, associated software and remote management device (e.g. computer). Software is customizable for specific applications, is menu-driven and user-friendly. For example, rotation of the biological production units attached to the carousel may be defined by user set programs for precise control of movement and positioning of each biological production unit. The carousel can be operable from a central workstation or remote management device. A convenient user actuated touch pad screen device may be used and connected to each of the biological production units operationally connected to a central computer.

According to an aspect of the invention, is an upright carousel for translating a plurality of biological units in unison along a vertical elliptical orbit while maintaining each individual biological load stable relative to gravity, and providing for individual dynamic axial rotation of any one or all of the biological units.

In aspects, the carousel comprises a spacing adjustment means to adjust the spacing of each biological unit relative to adjacent biological units so as to maximize the spatial density of biological units in selected zones of the carousel by close spacing and enhance user access to biological units in other selected zones by open spacing.

In aspects, each of the biological units are independently operable and linked to a central source of operational resources.

In aspects, the biological loads are sensitive to orientation relative to gravity.

In aspects, the carousel comprises an upright drive track and a support track vertically offset from one another and held together by a plurality of linkage mechanisms, each of the linkage mechanisms adapted to support a biological unit during translational movement along the elliptical orbit of the drive track and support track.

In aspects, the biological units are supported in a cantilevered position for ease of user access once positioned.

In aspects, the plurality of cantilevered biological units are translationally positioned in unison along an upright frame comprising two vertically offset tracks. In aspects, the tracks are substantially oval. In aspects oval closed loops.

In aspects, the speed and direction of translation (clockwise or counter-clockwise) is user controlled and adjustable.

In aspects, alignment of each cantilevered biological unit is substantially maintained relative to gravity during translational movement of the units or when the carousel is stationary.

In aspects, the carousel provides dynamic adjustment of axial orientation (bi-directional) relative to gravity of each independent cantilevered biological unit during translational movement of the units or when stationary.

In aspects, precise positioning of each cantilevered biological unit is user controlled for ergonomic access.

In aspects, the cantilevered biological unit is a cantilevered biological production unit.

In aspects, the cantilevered biological production unit operationally supports an automated cell culture and/or tissue engineering system.

In aspects, each of the biological production units are independently operable to provide a customized cell culture and/or tissue engineering systems. In aspects, the cell culture and/or tissue engineering systems are for autologous cell therapies.

In aspects, the carousel reduces overall space/storage footprints while increasing employee safety and efficiency.

In aspects, the carousel is part of a system that further comprises a housing for vertical operational support of the carousel and means for connection of each biological production unit in succession to a central source of auxiliaries and resources.

In aspects of the invention is an automated carousel system for organizing, storing, and ergonomically accessing cell and/or tissue engineering systems enclosed in a biological production unit.

In aspects, the automated carousel and systems incorporating the carousel greatly increases facility biological operational capacity by fully utilizing overhead space to recover up to 70% of the floor space required by conventional biological culturing systems.

According to an aspect of the invention is an automated vertical track assembly for supporting a plurality of biological units, wherein the carousel is configured for:

(i) user operated start and stop of translational movement of the biological units in unison along a defined path of the vertical track while maintaining each of the biological units properly oriented with respect to gravity; and (ii) user operated start and stop of axial rotation of individual biological units;

wherein during both (i) and (iii) each of the biological units is independently operable support a customized automated cell and tissue culture system therein; and wherein each of said biological units is interlinked to share a central source of operational resources.

According to an aspect of the invention is a vertical carousel comprising a plurality of biological units substantially geometrically constrained to translationally move in unison in a vertical elliptical orbit while maintaining the proper orientation of each of the plurality of biological units with respect to gravity, and separately axially rotating any independent one or more of the plurality of biological units.

According to another aspect of the invention is a vertical carousel comprising:
 a plurality of biological units substantially geometrically constrained for translational movement along a vertical elliptical orbit in unison while maintaining a stable orientation of each of the plurality of biological units with respect to gravity, and for separate axial rotation of any one or more of the plurality of biological units;
 means to control the translational movement of the biological units for user positioning; and
 means to actuate the axial rotation of the any one or more of the plurality of biological units.

According to an aspect of the invention is an automated carousel comprising:
 a vertical track assembly comprising a drive track and a support track vertically offset from one another;
 a plurality of translation assemblies connecting the drive track and the support track at spaced apart positions, each translation assembly supporting a cantilevered biological unit, wherein said plurality of translation assemblies is configured for providing (i) translational movement along the connected tracks in unison while maintaining the proper orientation of each cantilevered biological unit with respect to gravity, and separately, (ii) axial rotation of each biological unit.

According to an aspect of the invention is a system for maximizing cell and/or tissue engineering production, the system comprising a plurality of automated carousels as described herein supported and arranged in series.

According to a further aspect of the invention is a method for maximizing cell and/or tissue engineering production, the method comprising providing a series of the automated carousel system as described herein in a production facility.

According to a further aspect of the invention is a translation assembly for a vertical carousel having a drive track and vertically off set support track, for supporting a biological unit for translational movement and independent axial rotation, the translation assembly comprising:
 a first end defining a reversible coupling for receiving an input shaft of a biological unit;
 a central hub comprising:
  an outer hub shell supporting a drive carriage cooperatively engaged with the drive track for translational movement thereon, and
  an inner hub comprising a separate mechanism configured for the axial rotation of the biological unit; and
 a second end having a vertically downward extending resistance arm mounted via the inner hub and at its vertically lowest point a pivotally connected support carriage cooperatively engaged with the support track for translational movement thereon, wherein the vertically extending resistance arm prevents rotation of the inner hub and is maintained in a vertical orientation by geometrical constraint arising from the fixed vertical offset of the drive track and support track during translational movement along the tracks.

According to an aspect of the invention is an automated carousel system for the distribution and ergonomic positioning of multiple biological production units each of the units comprising an automated individually operable cell and/or tissue culture system, the automated carousel system comprising:
 an automated carousel comprising:
  a vertical track assembly comprising a drive track and a support track vertically offset therefrom;
  a plurality of translation assemblies connecting the drive track and the support track at spaced apart positions, each of said plurality of translation assemblies supporting a cantilevered biological production unit, wherein said plurality of translation assemblies is configured for providing (i) translational movement along the connected tracks in unison while maintaining the proper orientation of each cantilevered biological production unit with respect to gravity, and separately, (ii) axial rotation of each biological production unit;
 means for independent biological control of each cell and/or tissue culture system within each of said biological production units;
 a vertical housing assembly supporting the carousel, the housing assembly comprising a central source of operational resources;
 means for interconnecting the central source of operational resources to each successive biological production unit; and
 computer connection.

According to an aspect of the invention is a method for improving ergonomics for users of an automated carousel system that comprises a plurality of independent culture systems each supported within a biological production unit, the method comprising:
 mounting a plurality of biological production units on an automated carousel comprising:
  a vertical track assembly comprising a drive track and a support track vertically offset therefrom;
  a plurality of translation assemblies connecting the drive track and the support track at spaced apart positions, each of said plurality of translation assemblies supporting a cantilevered biological production unit, wherein said plurality of translation assemblies is configured for providing (i) translational movement along the connected tracks in unison while maintaining the proper orientation of each cantilevered biological production unit with respect to gravity, and separately, (ii) axial rotation of each biological production unit;
 wherein (i) and (ii) is user controlled for ergonomic access to each biological production unit by a user.

According to a further aspect of the invention is a method for increasing biological production capacity utilizing cell and/or tissue culture systems in a production facility, the method comprising:
 supporting a plurality of biological production units each housing a cell and/or tissue culture system on an upright automated carousel, the carousel comprising a plurality of translation assemblies connecting a drive track and a support track at spaced apart positions, each of said plurality of translation assemblies supporting a cantilevered biological production unit, wherein said plurality of translation assemblies is configured for providing (i) translational movement along the connected tracks in unison while maintaining the proper orientation of each cantilevered biological production unit with respect to gravity, and separately, (ii) axial rotation of each biological production unit.

According to a further aspect of the invention is an ergonomic automated carousel for supporting automated individually operable biological systems, the carousel comprising:

a plurality of translation assemblies connecting a drive track and a support track at spaced apart positions, each of said plurality of translation assemblies supporting a cantilevered biological production unit, wherein said plurality of translation assemblies is configured for providing (i) translational movement along the connected tracks in unison while maintaining the proper orientation of each cantilevered biological production unit with respect to gravity, and separately, (ii) axial rotation of each biological production unit; and means to select translationally move any one of the biological production units along the connected track to a specific position to accommodate a user for ergonomic inspection by said user.

According to a further aspect of the invention is a method for ergonomically positioning an automated selected cell culture and/or tissue engineering system for inspection by a user, the method comprising:

sending one or more translational movement operating instructions to an upright carousel comprising a plurality of spaced apart cantilevered biological production units configured to contain the cell and/or tissue culture system for translationally moving the plurality of cantilevered biological production units in unison via a remote management device, the one or more translational movement instructions comprising information about the location on the carousel of a target biological production unit for positioning and information regarding physical measurement specifications of a specific user standing or seated, the carousel comprising a controller and a communication interface, the controller being configured to:

(i) receive the one or more rotation operating instructions from a remote management device via the communication interface, (ii) operate the carousel for translational movement of the plurality of cantilevered biological production units, while maintaining proper orientation relative to gravity of each of the cantilevered biological production units during translational movement or when stationary, (iii) adjust axial orientation relative to gravity of any one or more of the plurality of cantilevered biological production units during translational movement or when stationary, (iv) identify the target biological production unit for ergonomic positioning for the specific user, (v) position the target biological production unit according to the physical measurements of the specific user standing or seated, and send one or more results of (i)-(v) to the remote management device via the communication interface, receive instructions from the remote management device via the communication interface of the carousel to operate the carousel for translational movement to ergonomically position the target biological production unit to the physical measurement specifications of the specific user, stopping the translational movement operating instructions when the target biological production unit is ergonomically positioned, and sending one or more results of the ergonomic positioning to the remote management device via the communication interface of the carousel.

In any of the aforementioned aspects, one of skill in the art recognizes that the automated upright carousel can operationally support any desired number of biological production units such as at least two biological production units, up to about six units, up to about eight units, up to about 10 units, up to about 12 units, up to about 14 units, up to about 16 units, up to about 18 units or up to about 20 units or more.

The automated carousel enables ergonomic access to a specific independent cell and/or tissue culture system without disturbance of the biological processes underway in any of the other independent multiple cell and/or tissue culture systems. The carousel is generally height adjustable and easily configurable to a wide variety of user sizes, shapes and weights. The ergonomic carousel is configured to alleviate existing muscular, skeletal or nervous system issues and/or configured to prevent such issues in the first instance for laboratory personnel. In embodiments, the ergonomic carousel is suitable for vertical adjustment for a sitting configuration to a standing configuration or vice-versa.

A1. An automated vertical track assembly for supporting a plurality of biological units, wherein the vertical track assembly is configured for:

(i) user operated start and stop of translational movement of the biological units in unison along a defined path of the vertical track assembly while maintaining each of the biological units properly oriented with respect to gravity; and (ii) user operated start and stop of axial rotation of individual biological units;

wherein during both (i) and (iii) each of the biological units is independently operable to support a customized automated cell and tissue culture system therein; and wherein each of said biological units is interlinked to share a central source of operational resources.

A2. A vertical carousel comprising a plurality of biological units substantially geometrically constrained to translationally move in unison in a predefined orbit while maintaining the proper orientation of each of the plurality of biological units with respect to gravity, and separately axially rotating any independent one or more of the plurality of biological units.

A3. A vertical carousel comprising a plurality of biological units substantially geometrically constrained to translationally move in unison in a predefined orbit while maintaining the proper orientation of each of the plurality of biological units with respect to gravity, and separately the ability to adjust the spacing of each biological unit relative to adjacent biological units so as to maximize the spatial density of biological units in selected zones of the carousel by close spacing and enhance user access to biological units in other selected zones by open spacing.

A4. A vertical carousel comprising:
- a plurality of biological units substantially geometrically constrained for translational movement along a vertical elliptical orbit in unison while maintaining a stable orientation of each of the plurality of biological units with respect to gravity, and for separate axial rotation of any one or more of the plurality of biological units;
- means to control the translational movement of the biological units for user positioning; and
- means to actuate the axial rotation of the any one or more of the plurality of biological units during translational movement or when stationary.

1. An automated carousel comprising:
- a vertical track assembly comprising a drive track and a support track vertically offset from one another;
- a plurality of translation assemblies connecting the drive track and the support track at spaced apart positions, each translation assembly supporting a cantilevered biological unit, wherein said plurality of translation assemblies is configured for providing (i) translational movement along the connected tracks in unison while maintaining the proper orientation of each cantilevered biological unit with respect to gravity, and separately, (ii) axial rotation of each biological unit.

1a. The automated carousel of claim 1a, wherein each of the plurality of translation assemblies is a horizontal hub assembly.

1b. The automated carousel of claim 1a, wherein said horizontal hub assembly comprises:
a first end defining a reversible coupling for receiving an input shaft of the cantilevered biological unit;
a central hub comprising:
an outer hub shell supporting a drive carriage cooperatively engaged with the drive track for translational movement thereon, and
an inner hub comprising a separate mechanism configured for the axial rotation of the biological unit; and
a second end having a vertically downward extending resistance arm mounted via the inner hub and at its vertically lowest point a pivotally connected support carriage cooperatively engaged with the support track for translational movement thereon, wherein the vertically extending resistance arm prevents rotation of the inner hub and is maintained in a vertical orientation by geometrical constraint arising from the fixed vertical offset of the drive track and support track during translational movement along the tracks.

2. The automated carousel of claim 1b, wherein the reversible coupling is a cantilevered coupling that extends laterally.

2a. The automated carousel of claim 1b, 2 or 2a, wherein during translational movement at track bends, the outer hub shell and affixed drive carriage undergo rotation and inversion while simultaneously the corresponding support carriage pivots from a vertical to a horizontal position, both drive carriage and support carriage remaining cooperatively engaged with their respective tracks and wherein the resistance arm remains vertically downwardly orientated.

3. The automated carousel of any one of claims 1b, 2 or 2a, wherein the separate mechanism in the inner hub comprises a motor driven central shaft for engaging with the input shaft of the biological unit, wherein actuation of the motor actively rotates the central shaft at a controlled speed causing axial rotation of the associated biological unit.

3a. The automated carousel of claim 3, wherein said axial rotation is intermittent or continuous.

3b. The automated carousel of claim 3, wherein said axial rotation is bi-directional.

4. The automated carousel of any one of claims 1b, 2, 2a or 3, wherein said drive carriage comprises a drive block assembly with one face thereof comprising affixed vertically arranged pairs of outwardly projecting bearing members for gripping the drive track and for engaging with a drive means adapted to move along the course of travel defined by the drive track.

5. The automated carousel of any one of claims 1b, 2, 2a, 3 or 4, wherein said support carriage comprises a support block assembly with one face thereof comprising affixed vertically arranged pairs of outwardly projecting bearing members for gripping the support track and for engaging with a drive means adapted to move along the course of travel defined by the track.

5a. The automated carousel of claim 4 or 5, wherein the translational movement of the support carriage is synchronous with the translational movement of the drive carriage.

6. The automated carousel of any one of claims 1b, 2, 2a, 3, 4 or 5, further wherein said second end of the horizontal hub assembly comprises a port for entry of a connection means for centrally provided operational resources to the biological unit.

7. The automated carousel of any one of claims 1b, 2, 2a, 3, 4, 5 or 6, wherein said port leads to a hollow shaft extending through the central hub to the biological unit.

8. The automated carousel of claim 7, wherein the connection means comprises cabling enclosing separate resources, the cabling originating from a central source and connecting each successive biological unit on said carousel.

9. The automated carousel of claim 8, wherein the operational resources are electrical supply lines, gas supply lines and controller connections.

10. The automated carousel of any one of claims 1 to 9, wherein the translational movement along the connected tracks is clockwise or counterclockwise.

11. The automated carousel of claim 10, wherein the translational movement along the connected tracks is about 180 degrees.

12. The automated carousel of claim 11, wherein speed of the translational movement is adjustable.

13. The automated carousel of claim 12, further operatively connected to a means for interrupting and/or stopping translational movement.

14. The automated carousel of any one of claims 1 to 13, wherein said cantilevered biological unit is a biological production unit.

15. The automated carousel of claim 14, wherein said biological production unit supports an individually operationally controlled cell and/or tissue engineering system.

16. The automated carousel of claim 15, wherein said cell and/or tissue engineering system performs one or more of: sterile reception/storage of tissue biopsy; automated monitoring of digestion process; digestion of biopsy tissue to yield disassociated cells; cell sorting and selection, safe waste collection; cell seeding on or within a proliferation substrate; scaffold proliferation of cells to expand cell populations; cell washing and cell collection; cell seeding on or within a tissue engineering scaffold or matrix; cell differentiation to allow specialization of cellular activity; tissue formation; mechanical and/or biochemical stimulation to promote tissue maturity; harvest of tissue engineered constructs/implants for reconstructive surgery; and storage and transportation of cells and implantable tissue.

17. The automated carousel of any one of claims 1 to 16, wherein said drive track and said support track are substantially oval, circular or elliptical.

18. The automated carousel of claim 17, wherein said drive track and said support track are oval.

19. The automated carousel of any one of claims 1 to 18, wherein comprising up to 24 translation assemblies each supporting a cantilevered biological unit.

19a. The automated carousel of any one of claims 1 to 19, further comprising means to adjust spacing of each biological unit relative to adjacent biological units so as to maximize the spatial density of biological units in selected zones of the carousel by close spacing and enhance user access to biological units in other selected zones by open spacing.

19b. The automated carousel of any one of claims 1 to 19a, wherein the adjustment of spacing can be during translational movement of the biological units or when stationary.

20. An automated system for maximizing cell and/or tissue engineering production, the system comprising an automated carousel of any one of claims 1 to 19 supported within a vertical housing and operationally connected to one or more controllers for control of translation movement by a user and precise ergonomic positioning of the biological unit for inspection thereof.

21. The system of claim 20, comprising a plurality of the automated carousels arranged in series.

21. An automated carousel system for the distribution and ergonomic positioning of multiple biological production units each of the units comprising an automated individually operable cell and/or tissue culture system, the automated carousel system comprising:
  an automated carousel comprising:
  a vertical track assembly comprising a drive track and a support track vertically offset therefrom;
  a plurality of translation assemblies connecting the drive track and the support track at spaced apart positions, each of said plurality of translation assemblies supporting a cantilevered biological production unit, wherein said plurality of translation assemblies is configured for providing (i) translational movement along the connected tracks in unison while maintaining the proper orientation of each cantilevered biological production unit with respect to gravity, and separately, (ii) axial rotation of each biological production unit;
  means for independent biological control of each cell and/or tissue culture system within each of said biological production units;
  a vertical housing assembly supporting the carousel, the housing assembly comprising a central source of operational resources;
  means for interconnecting the central source of operational resources to each successive biological production unit; and
  computer connection.

22. The automated carousel system of claim 21, wherein each biological production unit comprises a connected interface for communication by a user, said connected interface connected to the computer.

23. The automated carousel system of claim 21 or 22, wherein the upright frame comprises up to 24 translation assemblies.

24. The automated carousel system of claim 21, wherein the vertical housing assembly comprises a base with retractable wheels.

25. A method for maximizing cell and/or tissue engineering production, the method comprising providing one or more automated carousels system of any one of claims 1 to 19 in a production facility.

26. A method for improving ergonomics for users of an automated carousel system that comprises a plurality of independent culture systems each supported within a biological production unit, the method comprising:
  mounting a plurality of biological production units on an automated carousel comprising:
  a vertical track assembly comprising a drive track and a support track vertically offset therefrom;
  a plurality of translation assemblies connecting the drive track and the support track at spaced apart positions, each of said plurality of translation assemblies supporting a cantilevered biological production unit, wherein said plurality of translation assemblies is configured for providing (i) translational movement along the connected tracks in unison while maintaining the proper orientation of each cantilevered biological production unit with respect to gravity, and separately, (ii) axial rotation of each biological production unit;
  wherein (i) and (ii) is user controlled for ergonomic access to each biological production unit by a user.

27. A method for increasing biological production capacity utilizing cell and/or tissue culture systems in a production facility, the method comprising:
  supporting a plurality of biological production units each housing a cell and/or tissue culture system on an upright automated carousel, the carousel comprising a plurality of translation assemblies connecting a drive track and a support track at spaced apart positions, each of said plurality of translation assemblies supporting a cantilevered biological production unit, wherein said plurality of translation assemblies is configured for providing (i) translational movement along the connected tracks in unison while maintaining the proper orientation of each cantilevered biological production unit with respect to gravity, and separately, (ii) axial rotation of each biological production unit.

28. An ergonomic automated carousel for supporting automated individually operable biological systems, the carousel comprising:
  a plurality of translation assemblies connecting a drive track and a support track at spaced apart positions, each of said plurality of translation assemblies supporting a cantilevered biological production unit, wherein said plurality of translation assemblies is configured for providing (i) translational movement along the connected tracks in unison while maintaining the proper orientation of each cantilevered biological production unit with respect to gravity, and separately, (ii) axial rotation of each biological production unit; and
  means to select translationally move any one of the biological production units along the connected track to a specific position to accommodate a user for ergonomic inspection by said user.

29. A method for ergonomically positioning an automated selected cell culture and/or tissue engineering system for inspection by a user, the method comprising:
  sending one or more translational movement operating instructions to an upright carousel comprising a plurality of spaced apart cantilevered biological production units configured to contain the cell and/or tissue culture system for translationally moving the plurality of cantilevered biological production units in unison via a remote management device, the one or more translational movement instructions comprising information about the location on the carousel of a target biological production unit for positioning and information regarding physical measurement specifications of a specific user standing or seated,
  the carousel comprising a controller and a communication interface, the controller being configured to:
  (i) receive the one or more rotation operating instructions from a remote management device via the communication interface,
  (ii) operate the carousel for translational movement of the plurality of cantilevered biological production units, while maintaining proper orientation relative to gravity of each of the cantilevered biological production units during translational movement or when stationary,
  (iii) adjust axial orientation relative to gravity of any one or more of the plurality of cantilevered biological production units during translational movement or when stationary,
  (iv) identify the target biological production unit for ergonomic positioning for the specific user,
  (v) position the target biological production unit according to the physical measurements of the specific user standing or seated, and
  send one or more results of (i)-(v) to the remote management device via the communication interface, receive instructions from the remote management device via the communication interface of the carousel to operate the carousel for translational movement to ergonomically position the target biological production unit to the physical measurement specifications of the specific user, stopping the translational movement operating instructions when the target biological production unit is ergonomically positioned, and sending one or more results of the ergonomic positioning to the remote management device via the communication interface of the carousel.

BRIEF DESCRIPTION OF DRAWINGS

The following description of typical aspects described herein will be better understood when read in conjunction with the appended drawings. For the purpose of illustrating the invention, there are shown in the drawings aspects which are presently typical. It should be understood, however, that the invention is not limited to the precise arrangements and instrumentalities of the aspects shown in the drawings. It is noted that like reference numerals refer to like elements across different embodiments as shown in the drawings and referred to in the description.

The description herein will be more fully understood in view of the following drawings.

DESCRIPTION

Figure 1:
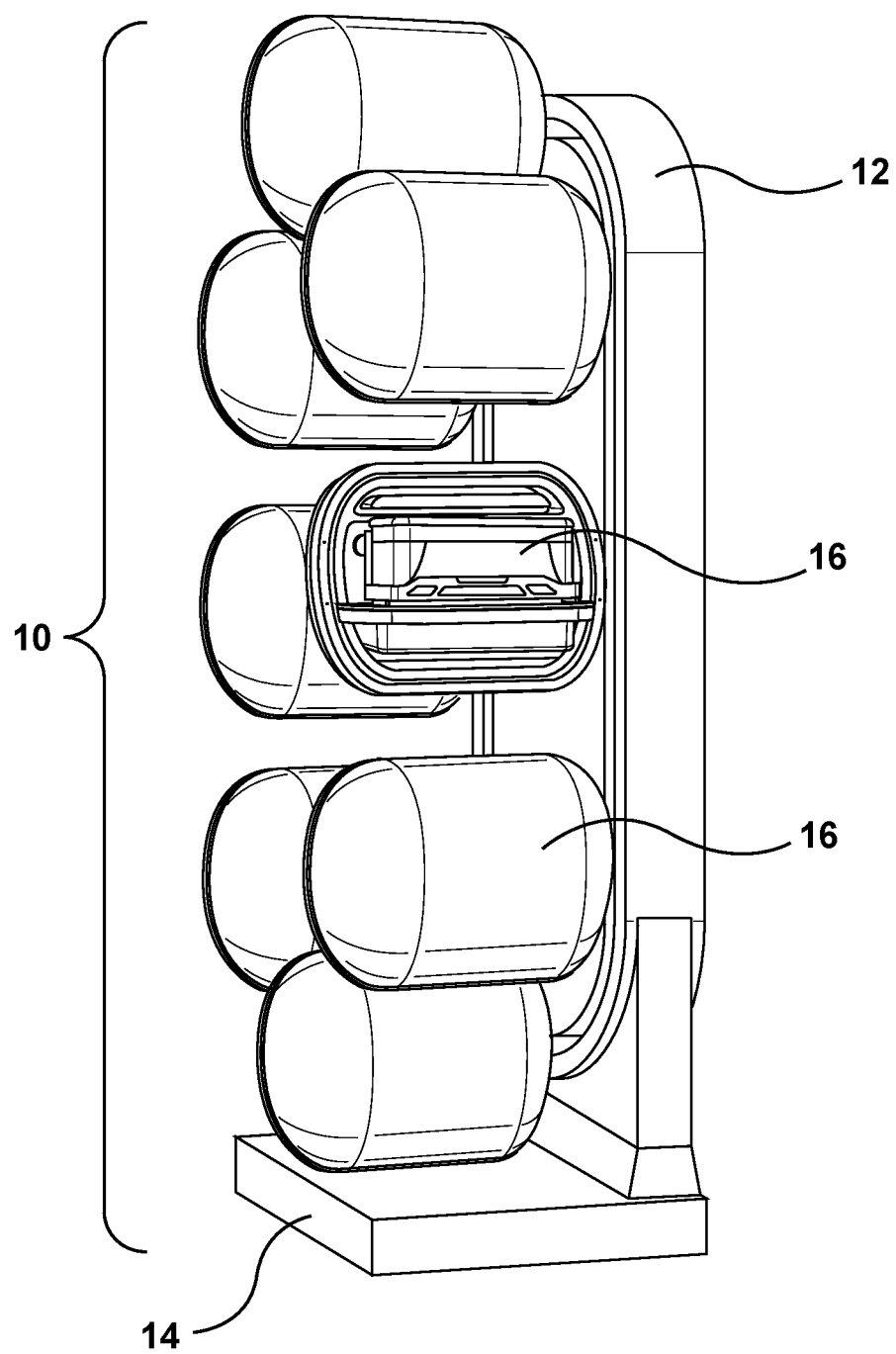
FIG. 1 shows one non-limiting configuration of a carousel system that comprises a carousel of the invention supported on a vertical housing having a support base and supporting a number of vertically positioned biological production units. One of the biological production units is in an open configuration.

All publications, patent applications, patents, and other references mentioned herein are incorporated by reference in their entirety. The publications and applications discussed herein are provided solely for their disclosure prior to the filing date of the present application. Nothing herein is to be construed as an admission that the present invention is not entitled to antedate such publication by virtue of prior invention. In addition, the materials, methods, and examples are illustrative only and are not intended to be limiting.

In the case of conflict, the present specification, including definitions, will control.

Unless defined otherwise, all technical and scientific terms used herein have the same meaning as is commonly understood by one of skill in the art to which the subject matter herein belongs. As used herein, the following definitions are supplied in order to facilitate the understanding of the present invention.

As used herein, the articles "a" and "an" preceding an element or component are intended to be non-restrictive regarding the number of instances (i.e. occurrences) of the element or component. Therefore, "a" or "an" should be read to include one or at least one, and the singular word form of the element or component also includes the plural unless the number is obviously meant to be singular.

As used herein, the terms "invention" or "present invention" are non-limiting terms and not intended to refer to any single aspect of the particular invention but encompass all possible aspects as described in the specification and the claims.

As used herein the terms 'comprises', 'comprising', 'includes', 'including', 'having' and their inflections and conjugates denote 'including but not limited to' and are to be understood to be open-ended, e.g., to mean including but not limited to.

As used herein, the term "about" refers to variation in the numerical quantity. In one aspect, the term "about" means within 10% of the reported numerical value. In another aspect, the term "about" means within 5% of the reported numerical value. Yet, in another aspect, the term "about" means within 10, 9, 8, 7, 6, 5, 4, 3, 2, or 1% of the reported numerical value.

Should a range of values be recited, it is merely for convenience or brevity and includes all the possible sub-ranges as well as individual numerical values within and about the boundary of that range. Any numeric value, unless otherwise specified, includes also practical close values and integral values do not exclude fractional values. Sub-range values and practically close values should be considered as specifically disclosed values.

It will be understood that any component defined herein as being included may be explicitly excluded from the claimed invention by way of proviso or negative limitation.

As may be used herein the terms 'close', 'approximate' and 'practically' denote a respective relation or measure or amount or quantity or degree that has no adverse consequence or effect relative to the referenced term or embodiment or operation or the scope of the invention.

As may be used herein any terms referring to geometrical relationships such as 'vertical', 'horizontal', 'parallel', 'opposite', 'straight', "lateral", "parallel", "perpendicular" and other angular relationships denote also approximate yet functional and/or practical, respective relationships.

As used herein "vertical" can be interchanged with "upright". As used herein "substantially vertical" or "substantially upright" is used to refer to an orientation where the track assemblies and support tracks described herein are suitably perpendicular (i.e., form a 90° angle relative to) to the ground or a floor of a warehouse, building, or production facility, but also includes embodiments where the tracks are within about 0°-60° from perpendicular. That is in embodiments, substantially vertical allows for the tracks to be tilted from perpendicular at an angle of about 5°, 10°, about 20°, about 30°, about 45°, etc.

As used herein "translational movement" refers to the movement of an object from one place to another without a change in its orientation relative to a fixed point, as opposed to rotation, in which the object is turning about an axis. With respect to the carousel of the invention, the carousel provides translational movement of multiple biologic production units along a substantially vertical curved path of the carousel while maintaining each individual unit fixed (i.e. horizontal, stable) with respect to its orientation to gravity. "Translational movement" can be bi-directional.

As used herein, "translates" or "translational" refers to the movement of a load supported on the carousel structure of the invention where the carousel comprises two tracks of the same size and shape that are oval, elliptical, spherical, orbital, capsule-shaped and the like. "Translate along the tracks" can be interchanged with "translation along the tracks" both meaning the movement from one position to a second position along the oval path of the upright carousel, wherein the translation does not invoke rotational inversion (of a supported unit and contents therein) during movement/travel along such frame.

As used herein, "rotation" or 'axial rotation' refers to movement of an object turning about its central axis. With respect to individual dynamic adjustment of axial rotation of a biological production unit, this means that the biological production unit rotates about its axis. This can be bi-directional. This can also be referred to as "rocking motion" or "tilt".

As used herein, a "user" is interchangeable with an "operator".

As may be used herein, the terms 'preferred', 'preferably', 'typical', 'typically' or 'optionally' do not limit the scope of the invention or embodiments thereof.

As may be used herein the term 'substantially' (or synonyms thereof) denote with respect to the context a measure or extent or amount or degree that encompass a large part or most of a referenced entity, or an extent at least moderately or much greater or larger or more effective or more important relative to a referenced entity or with respect to the referenced subject matter.

As used herein the term 'may' denotes an option or an effect which is either or not included and/or used and/or implemented and/or occurs, yet the option constitutes at least a part of some embodiments of the invention or consequence thereof, without limiting the scope of the invention.

The phrase "and/or," as used herein in the specification and in the claims, should be understood to mean "either or both" of the elements so conjoined, e.g., elements that are conjunctively present in some cases and disjunctively present in other cases. Other elements may optionally be present other than the elements specifically identified by the "and/or" clause, whether related or unrelated to those elements specifically identified unless clearly indicated to the contrary.

As used herein in the specification and in the claims, "or" should be understood to have the same meaning as "and/or" as defined above. For example, when separating items in a list, "or" or "and/or" shall be interpreted as being inclusive, e.g., the inclusion of at least one, but also including more than one, of a number or list of elements, and, optionally, additional unlisted items. In general, the term "or" as used herein shall only be interpreted as indicating exclusive alternatives (e.g. "one or the other but not both") when preceded by terms of exclusivity, such as "either," "one of" "only one of" or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

As used herein "a plurality" is understood to be any number greater than one. "Plurality" means "two or more".

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

It should also be understood that, unless clearly indicated to the contrary, in any methods claimed herein that include more than one step or act, the order of the steps or acts of the method is not necessarily limited to the order in which the steps or acts of the method are recited.

As used herein, "unit" is a biological unit or biological production unit. Unit is meant to generically define a biological structure used for supporting cell and tissue culture systems therein.

As used herein "cantilevered unit" or "cantilevered biological production unit" are interchangeable as they refer to the same part.

As used herein, "biological production unit" comprises an independently operable automated cell culture and/or tissue engineering platform/system comprising components for multifunctional operation of one or more of cell culture, cell seeding, cell digestion, cell growth, cell differentiation, cell expansion, tissue culture and tissue growth.

The biological production unit may house and support an automated, portable, operationally multifunctional cell culture and/or tissue engineering system that performs/provides one or more of the following: sterile reception/storage of tissue biopsy; automated monitoring of digestion process; digestion of biopsy tissue to yield disassociated cells; cell sorting and selection, including safe waste collection; cell seeding on or within a proliferation substrate or scaffold proliferation of cells to expand cell populations; cell washing and cell collection; cell seeding on or within a tissue engineering scaffold or matrix; cell differentiation to allow specialization of cellular activity; tissue formation; mechanical and/or biochemical stimulation to promote tissue maturity; harvesting the tissue engineered constructs/implants for reconstructive surgery; and storage and transportation of implantable tissue.

In aspects this may be a tissue engineering cassette comprising one or more interlinked bioreactors that provide precise control at each stage. From cell source isolation and cell expansion through to cell collection, cell washing and final implant formation, the present system selectively combines key processes to meet the unique challenges of different autologous and allogeneic clinical applications of cell and tissue therapy. Embedded sensors provide real-time biofeedback and enable automatic adjustment in bioprocessing to accommodate natural variations in cell source behaviour. The entire bioprocess is contained within a disposable cassette to ensure maximum patient and operator safety and to streamline logistics. Suitable non limiting biological production units are described in U.S. Pat. Nos. 8,492,140; 9,701,932; 9,534,195; 9,499,780; and 9,783,768 (the contents of each of these U.S. patents is incorporated by reference in their entireties).

As used herein "automated cell culture system" is an automated system that comprises several operatively linked biological production units and processors.

As used herein "supported", "attached", "connected", "joined", "coupled", "linked", and "secured" may be interchangeably used with respect to the engagement of components of the carousel and components of systems and methods incorporating the invention. Further, any of these terms may be used with the term "reversibly".

A general non-limiting overview of the invention and practising the invention is presented below. The overview outlines exemplary practice of embodiments/aspects of the invention, providing a constructive basis for variant and/or alternative and/or divergent aspects/embodiments, some of which are subsequently described.

An effective and economical automation strategy is to adopt the use of process-specific bioreactors that can be controlled under automated sequences. Such bioreactors may be configured within a disposable, pre-sterilized cartridge or cassette for handling robustness and operator simplicity. Furthermore, the cassette and the related control instrumentation required for implementation of the automated sequences may be contained in an environmentally controlled enclosure (a biological production unit) to achieve the following (non-limiting) operational conditions:

1. Mechanical and electrical control interface for the specialized cassette;
2. Temperature control of environmental conditions for the biological manipulations of cells;
3. Gas control of environmental conditions for the biological manipulations of cells;
4. Independently controlled environment for the refrigerated storage of reagents;
5. Monitoring of critical process parameters; and
6. Electronic storage of process data consistent with data retention policies.

To address the objective of space-efficient organization and ergonomic access of multiple biological production units, an automated carousel was developed and described herein. The carousel is an upright carousel comprising a substantially vertical track assembly that supports and provides translational movement of a plurality of biological production units in unison or separately along the curved vertical track assembly for precise user positioning. The carousel suitably translates the supported biological production units simultaneously (i.e. in unison) along the curved vertical track assembly about ±180° vertical, in a clockwise or counter-clockwise direction, while maintaining a precise alignment/orientation of each of the biological production units relative to gravity. This ensures that any of the cell culture and/or tissue engineering systems supported within each of the biological production units is not negatively affected by changing the orientation of gravitational forces exerted thereon during the changing of the vertical positioning of the biological production units. The carousel also comprises a means for individually dynamically adjusting the axial rotation of any of the biological production units. Surprisingly, the translational and/or axial movement of individual biological production units supporting independently operable biological systems therein, does not compromise the interconnection of the units to a central source of operational resources. The carousel can also translate the supported biological production units separately. That is, rather than each moving in unison, a single unit can move, while the remaining units remain stationary (or substantially stationary), for example along a top or back of a carousel in a "bunched-up" or "collected" orientation. As desired, the next unit in line in the track can be separately translated out from the remaining units, allowing for work or inspection to be conducted on that unit.

The carousel is configured within a housing powered by connection with a power source and operatively connectable with a computer for operational control (e.g. remote device, via touchpad screen, via hand held device).

The carousel of the invention can be incorporated for use with a variety of automated cell and tissue culture systems.

FIG. 1 illustrates one non-limiting embodiment of the invention showing a configuration of an automated carousel system 1 that enables efficient consolidation of multiple independent cell production processes within an efficient spatial envelope. The carousel system 1 comprises an upright carousel 10 that is supported within a framework of a vertical housing assembly 12 that serves as the support frame and attachment structure for the carousel 10. The vertical housing assembly 12 is mounted on a base 14. The vertical housing assembly 12 provides for multiple functions including mechanical support and central delivery of auxiliaries and resources (e.g. power, gases, data, etc.) and workflow management. The carousel system 1 is illustrated as a "stand alone" structure requiring no additional support, and can be dimensioned to various sizes, as well as the corresponding size of the carousel, as is desired limited only by the vertical space of the particular industrial biological setting.

The carousel system 1 shows the scale up of biological production units supporting eight biological production units 16 on its common framework. The carousel 10 of the carousel system is shown to be substantially vertically configured to support eight individual and operationally independent biological production units 16 in an oval arrangement that follows the curved shape of the vertical carousel track frame (not shown) in a spatially close manner. One of the biological production units 16 is shown in an open configuration. The biological production units 16 are mounted to the carousel in a configuration for easy user access. In FIG. 1 this is shown to be in a cantilevered position allowing space for easy user access to the cell and tissue culture systems therein when the unit is opened. The biological production units 16 are translationally moved in unison or separately along the carousel track frame while maintaining their substantially even spacing and proper orientation with respect to gravity. As space is an important influence of efficiency in GMP (Good Manufacturing Practice) facilities, the automated carousel system not only takes advantage of the unused vertical space in a biological facility but is also structured to be compact by centrally housing operational resources within the housing assembly 12. This allows specific operational resource connections linking each of the biological production units in succession to be neatly stored and merge in a manifold style cabling system to a central source of operational resources (see FIG. 9). This configuration allows for the provision of resources to each biological production unit when the carousel is stationary or during translational and/or individual axial rotation of any biological unit.

Figure 2:
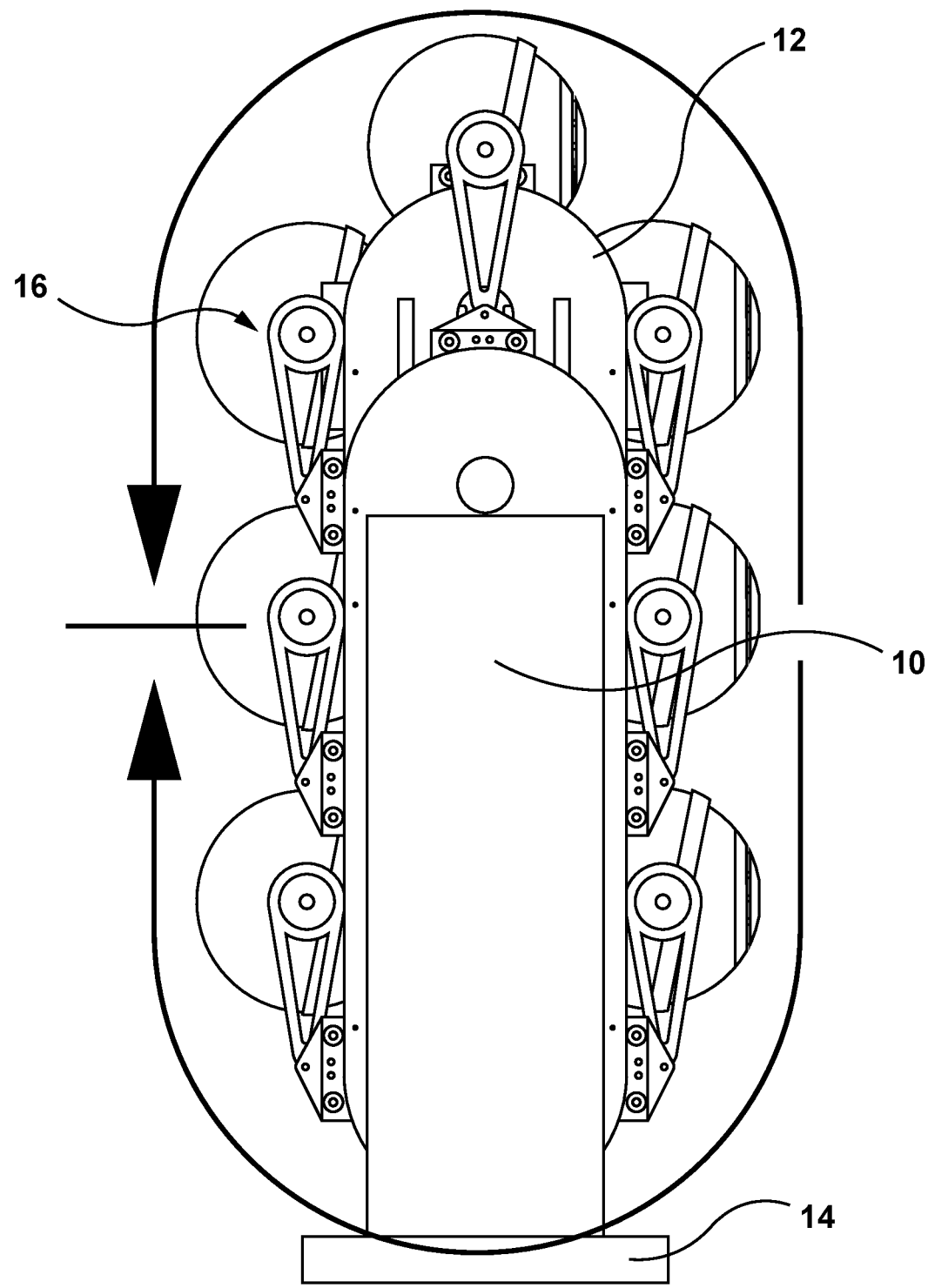
FIG. 2 is a side elevational view of the carousel system of FIG. 1, the arrows indicating that the carousel has about +/−180° vertical translational movement.

FIG. 2 shows that the carousel 10 can rotate a total of ±180 degrees during translational movement (indicated by arrows) along the carousel frame where every biological production unit 16 can be moved to any position relative to a preferred access point for an operator. Movement can be either clockwise or counter clockwise. Movement is precisely controlled directionally in increments and with respect to a selected desired speed. The translational movement of the biological production units along the carousel track is optionally constrained to about ±180 degrees to preclude any tendency to compromise the integrity of the cabling (not shown) that supply resources (e.g. power, data, gases, etc.) from a central location within the vertical housing assembly and to each of the individual biological production units in succession.

Figure 3:
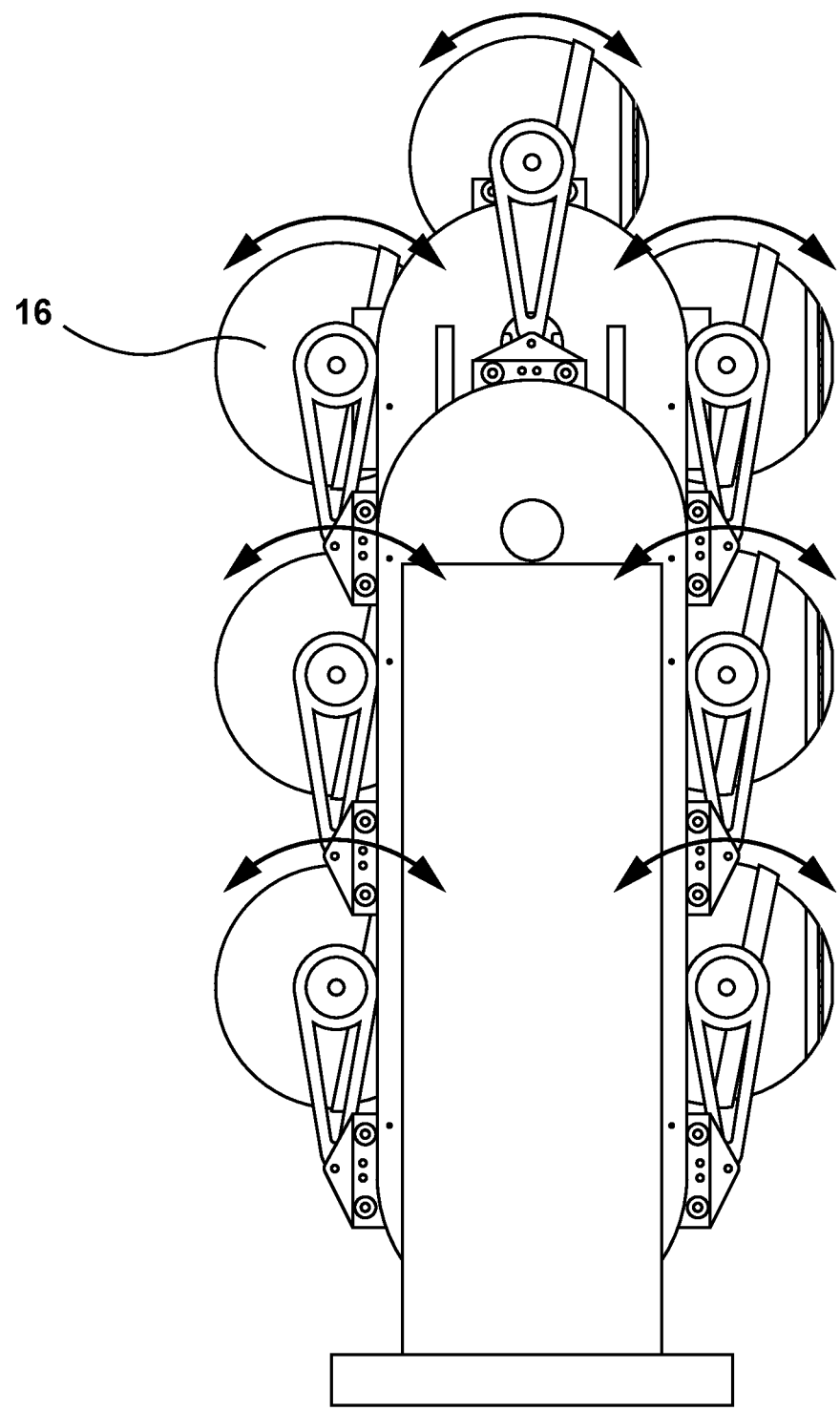
FIG. 3 is a side elevational view of the carousel system of FIG. 1, the arrows showing the individual axial rotation of each independent biological production unit.

Unlike conventional carousel designs for inventory management, mounting of the biological production units is important not only for efficient use of space but also for ensuring that the cell and tissue culture processes within each biological production unit is not negatively affected during translation of biological units along the vertical curved path of the carousel. The mounting also provides a further mechanism for additional dynamic control of the axial orientation of each individual biological production unit. FIG. 3 shows that each biological production unit 16 can be independently and dynamically adjusted with respect to its axial orientation relative to gravity (arrows) in a bi-directional manner through a defined range of angles (also referred to as "tilting" or "rocking"). Dynamic axial rotational adjustment of any one of the biological production units can be effected during the unison translational movement of the biological production units along the carousel or when the carousel is stationary.

Figure 4:
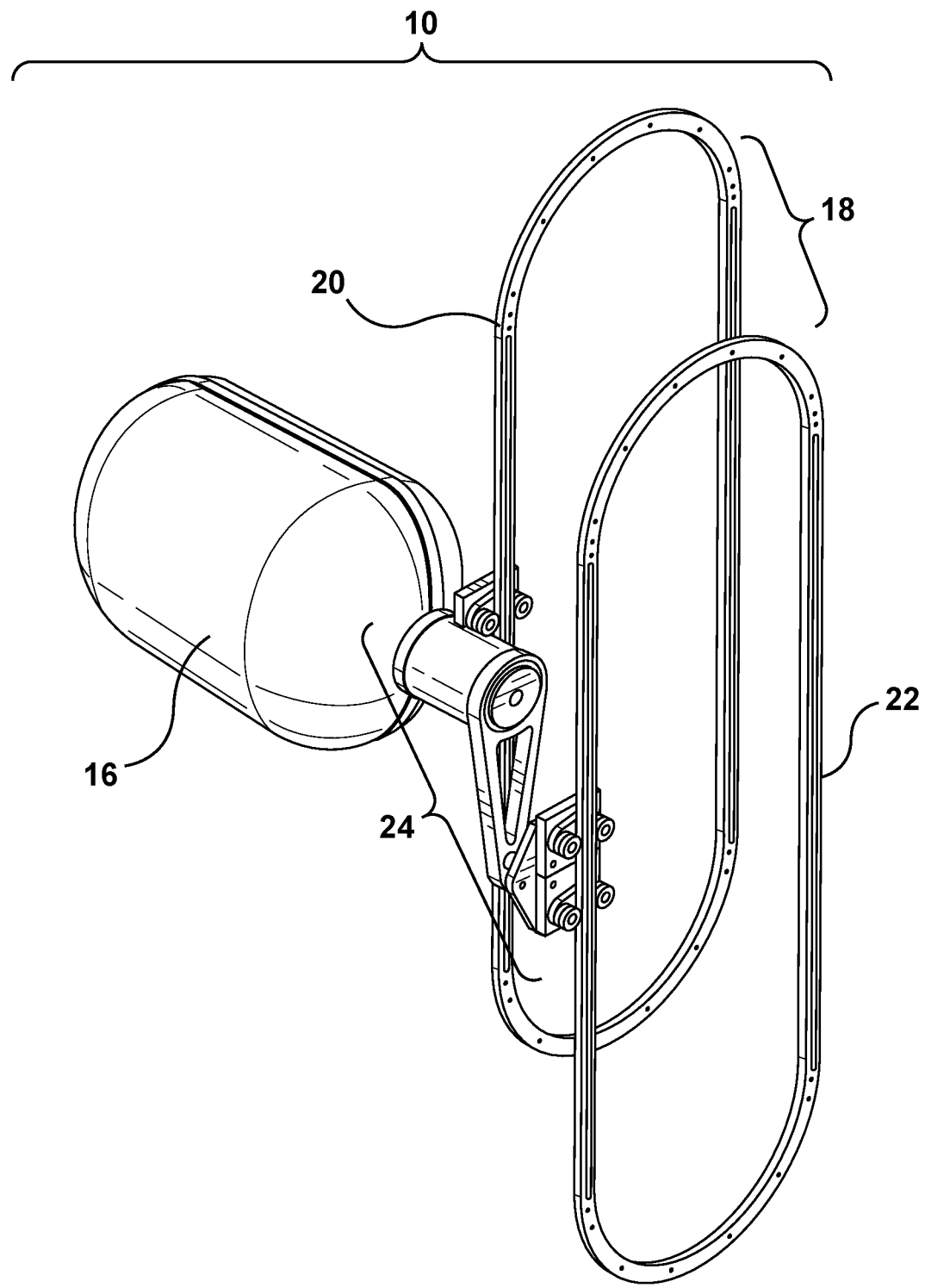
FIG. 4 shows the isolated carousel track structure supporting one representative biological production unit for simplicity.

FIG. 4 shows the structure of the carousel 10 of the invention supporting one cantilevered biological production unit 16 for simplicity. The carousel 10 is orientated upright (vertical) and comprises a track assembly 18 having a drive track 20 and a support track 22 that are spaced apart, substantially parallel to one another, and mechanically affixed to a rigid support frame (not shown). The carousel 10 can also be oriented substantially vertically, such that drive track 20 and support track are angled related to perpendicular, for example at an about of about 0°-60° relative to completely vertical (perpendicular to the ground or floor). Each of the drive track 20 and the support track 22 is shown to be oval (a closed loop) in shape and orientated so that the long runs of the loop extend vertically and the track bends are located on the top and bottom of the tracks. The drive track is positioned forwardly to the support track as it is coupled with the biological production unit that requires user access. The support track is spaced vertically lower with respect to the drive track. This vertical off-set is fixed.

A translation assembly 24 is shown that acts as the mechanical linkage connecting the drive track 20 and the support track 22 providing simultaneous translational movement along the connected tracks. The translation assembly is configured to couple with a biological production unit 16 at one end that is adjacent the drive track 20. The biological production unit 16 is shown to be individually mounted to the translation assembly 24 in a cantilevered position via a single cantilevered fixed reversible coupling (not shown). The translation assembly enables a cantilevered positioning of the biological production unit. The single attachment point for each cantilevered biological production unit enhances service access to each of the biological production units and further improves overall space efficiency. The cantilevered fixed reversible coupling allows for coupling and uncoupling such that any given biological production unit can be removed/detached from the arm assembly of the carousel and replaced or relocated to another position on the carousel. While one translation assembly is shown, is understood by one of skill in the art, that multiple translation assemblies are mounted in a desired spaced relationship linking the drive track to the support track each supporting a cantilevered biological production unit.

Operationally, the automated carousel must offer geometric stability by means of ensuring each production unit remains precisely aligned relative to the gravity vector throughout positional adjustment/rotation of the automated carousel. Systems where orientation is not critical employ the use of gravity as a mechanism for alignment, where the center of mass is lower than the pivot point of the object. However, such systems inadequately compensate for changes in the center of mass, which influences the position of the gravity vector relative to the object undergoing movement. The automated carousel described herein specifically orients the biological production unit relative to the gravity vector such that secondary operations within the biological production unit that influence the center of mass do not affect orientation relative to gravity. Furthermore, the resulting stability of the biological production unit(s) enables the movement of internal components relative to the gravity vector to achieve specific biological or fluidic events. In the case of specific production unit operations where a axial rotation is required, separate from the translation movement about the oval track of the automated carousel, an additional linkage is implemented for independent control of the orientation of the production unit (as shown in FIG. 3).

Figure 5:
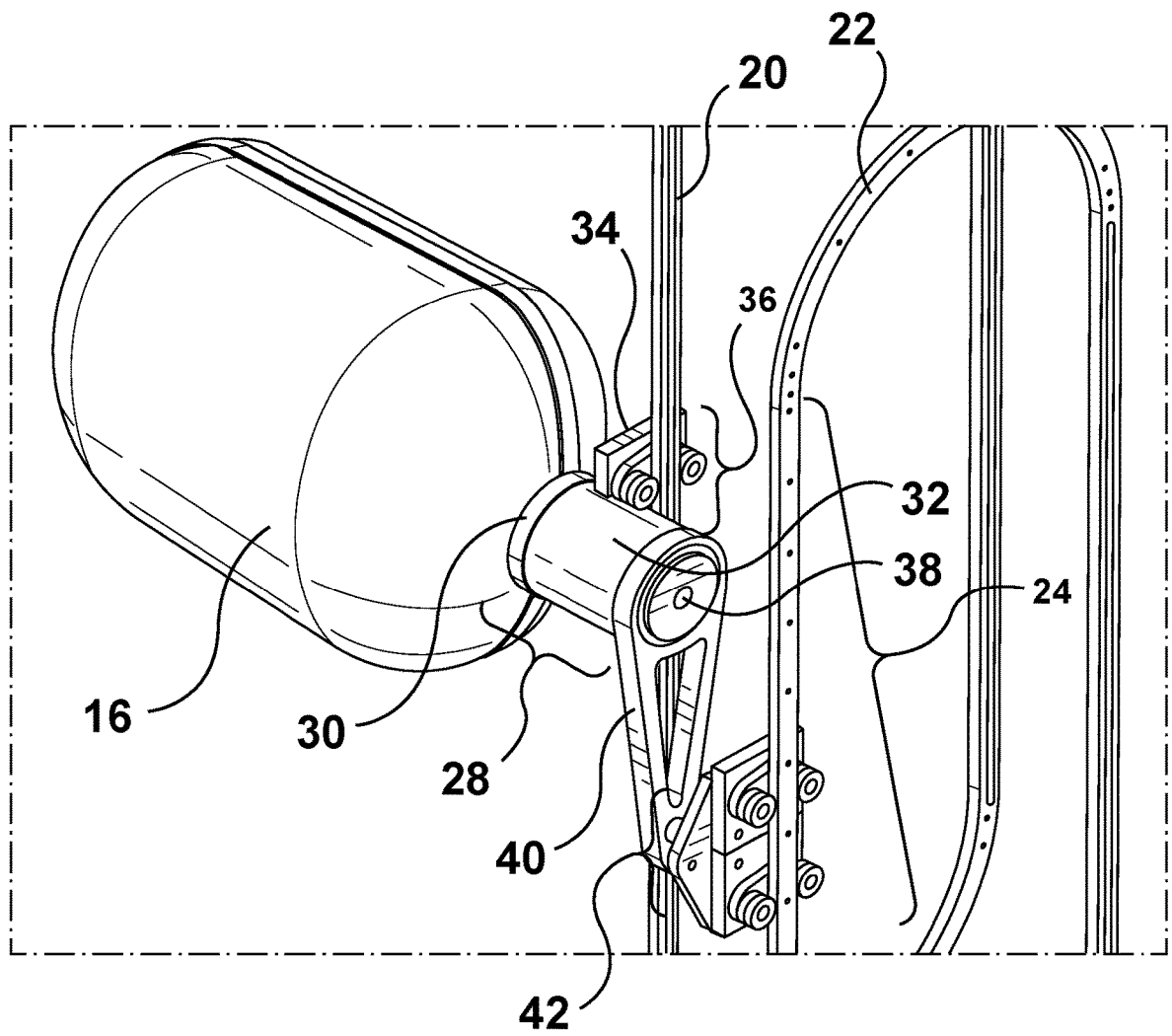
FIG. 5 shows a close up view of the isolated carousel track structure and mechanical linkage with the biological production unit.
Figure 6:
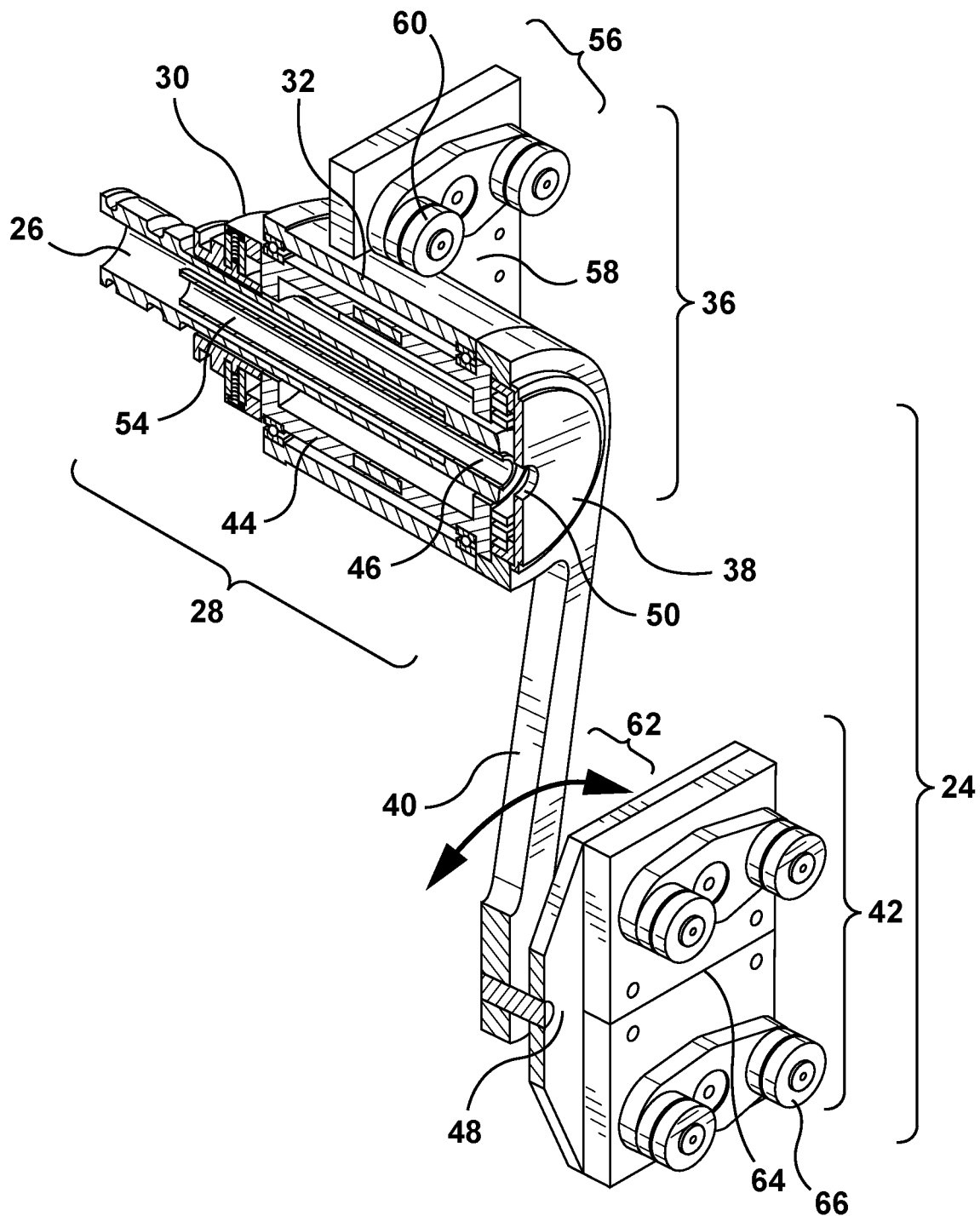
FIG. 6 shows the mechanical linkage structure of the carousel in isolation and with a central portion cut-away to show internal driving structures.

FIG. 5 more closely shows the structure of the translation assembly 24 is configured for synchronous translational movement along the tracks while supporting the biological production unit 16 in a cantilevered orientation. The translation assembly 24 comprises a horizontal hub assembly 28 having a first end 30 with a cantilevered fixed reversible coupling (not shown) that extends laterally to receive a shaft of the biological production unit 16. The horizontal hub assembly 28 also comprises a central hub 32 with a rigid extension 33 to support a drive carriage 36 that cooperatively engages the drive track 20 and its associated drive means (e.g. drive belt or drive linkage, not shown). The horizontal hub assembly has a second end 38 to which, via inner hub, is fixedly mounted a vertically downward extending resistance arm 40. The resistance arm 40 extends in a downwards orientation parallel to both tracks to which a support carriage 42 is affixed at its lowest end via a pivot mounting. The support carriage 42 cooperatively engages the support track 22 and its associated drive means (e.g. drive belt or drive linkage, not shown). The drive carriage and the support carriage travel synchronously around the oval tracks such that the resistance arm 40 is always maintained in a vertical orientation by virtue of a geometrical constraint arising from the fixed vertical offset of the drive track 20 and support track 22.

The use of a translation assembly to support the biological production unit enables the repositioning of the biological production unit to a location that is convenient for operator access to the cell and/or tissue culture system supported therein. While only one biological production unit is shown, a plurality of translation assemblies may be configured to travel along the tracks with each supporting a cantilevered biological production unit. The relative position of each translation assembly may be constrained by interconnecting linkages. Furthermore, it is feasible to provide adjustable spacing for the positions of the biological production units whereby spacing is exaggerated for locations where unconstrained operator access is required and reduced in locations where no operator access is required, such as the rear aspect of the carousel.

In addition to providing consistent vertical axis orientation of the biological production unit during translation along the tracks, the provision of the two mechanically and operationally linked carriages also provides the mechanical rigidity that is required to resist any bending moment imparted on the drive rack by the cantilevered biological production unit.

It is understood by one of skill in the art that the distance between the drive track and the support track may vary and this in part may be due to the size of the translation assembly providing linkage between the two tracks, the size and weight of the biological production units and the engineering forces required for adequate cantilevered mounting of multiple units. While the biological production units are shown cantilevered using a cantilevered mount, it is understood that other mounts with other orientations may be used. Furthermore, where only one biological production unit is shown to be cantilevered at each translation assembly, it is understood that smaller biological units may be used and thus more than one biological unit may be mounted in a cantilevered position, either in series or adjacent to each translation assembly.

It is also understood that the shape and size of the drive track and the support track should be substantively the same for proper translational movement along the carousel tracks and orientation with respect to gravity. While the tracks of the frame are shown to be substantially oval in shape, the shape can vary and is limited only by the ability to space apart the biological production units that are supported on the carousel and the ability to provide about ±180 degrees of rotational bidirectional movement. Therefore, the tracks can be substantially oval, substantially elliptical, substantially circular or substantially capsule-shaped. The carousel can be designed to be of any vertical height (e.g. size) limited by only the facility in which it will be used. The two tracks that make up the frame of the carousel can be may of any desired thickness and made of suitable materials that can withstand stress cycles and dynamic loading conditions during its use. Suitable materials comprise typically used engineering materials such as but not limited to metals and metal alloys (e.g. comprising high grade stainless steel, steel alloys, iron, copper, aluminum and combinations thereof).

FIG. 6 shows the translation assembly 24 in isolation with a portion of the central hub 32 cut away. The translation assembly 24 shows a central section that is a horizontal hub assembly 28. The first end 30 of the horizontal hub assembly has a cantilevered fixed reversible coupling 26 to mount a biological production unit. The central hub 32 has an outer hub shell 34 having one side affixed, via rigid extension, to a drive carriage 36 that cooperatively engages with the drive track for translational movement thereon. An inner hub 44 is retained via bearings within the outer hub shell 34. The inner hub 44 is constrained from rotating within the outer hub shell by way of the resistance arm 40 fixedly mounted to the inner hub and projecting vertically downward to connect with a support carriage 42 via a pivot connection and configured to cooperatively engage the support track 22 and its associated driven means (not shown). When the outer hub shell 34 undergoes rotational inversion while traveling the oval path of the primary track, the inner hub is constrained to maintain a consistent orientation relative to gravity by virtue of the attached resistance arm being constrained to remain vertical. This constraint on the orientation of the resistance arm occurs due to the cooperative positioning of the drive carriages and support carriages wherein the drive carriage is always positioned vertically above the secondary carriage when the carriages are traveling around the tracks.

The coupling 26 supporting the cantilevered biological production unit mechanically engages with a motor driven central shaft 54 within the inner hub 44 of the via bearings. The motor driven central shaft is either constrained from rotating within the inner hub 44 or actively rotated at a controlled speed by the motor drive and gearbox mounted on the inner hub that drives the axial rotational of the central shaft. Through the controlled orientation of the inner hub relative to gravity and the controlled orientation of the central shaft relative to the inner hub, it is possible to selectively axially rotate the central shaft and hence the biological production unit relative to gravity.

The drive carriage 36 is a drive block assembly 56 with one face thereof 58 having affixed vertically arranged pairs of outwardly projecting bearing members 60 for gripping the primary track 20 and engaging its associated drive means adapted translational movement along the course of travel defined by the primary track.

The support carriage 42 is a support block assembly 62 with one face thereof 64 having affixed vertically arranged pairs of outwardly projecting bearing members 66 for gripping the support track for moving along the course of travel defined by the support track. The support carriage actively translationally moves along the support track in a synchronous manner with the drive carriage while retaining the fixed vertical offset according to the length of the lever arm.

Although two pairs of bearings are shown on each of the primary carriage and support carriage (i.e. 60 and 66, respectively), it is understood by one of skill in the art that additional sets may be incorporated for additional gripping of either the primary track or the support track.

In operation, the translation assembly 24 and similar translation assemblies present on the tracks are moved in unison through physical connection of the primary carriage to a primary drive belt and motor assembly and a secondary drive belt linking the secondary carriages. The motion is a gliding motion with minimal friction based on the bearing interface between the carriages and the tracks. Furthermore, the carriages support significant lateral and bending loads. This load carrying capability and the use of two carriages offset via the translation assembly enables significant cantilever loads to be resisted thereby ensuring stable translation of the biological product units from position to position.

The biological production unit 16 is rigidly mounted to the translation assembly 24 via the cantilevered fixed reversible coupling 26 that cooperates with the motor driven central shaft 54 retained within the inner central hub 44. The inner central hub always maintains a consistent orientation relative to the gravity vector. The motor drive assembly positions the axial rotation of the central shaft 54 relative to the inner central hub. When the motor driven linkage 46 is dormant, the biological production unit (thus the cell and/or tissue culture system contained therein) will maintain a given orientation relative to the gravity vector. Through the activation of motor driven linkage 46, the axial position of central shaft 54 may be changed in either direction, thereby dynamically axially changing the position of the cell and/or tissue culture system relative to the gravity vector. This changing of the axial orientation of the biological production unit may be intermittent to aid a specific biological activity occurring within a cassette mounted within a biological production unit or may be continuous (e.g. rocking or tilting) of a bioreactor within the cassette housed in the biological production unit.

Figure 7:
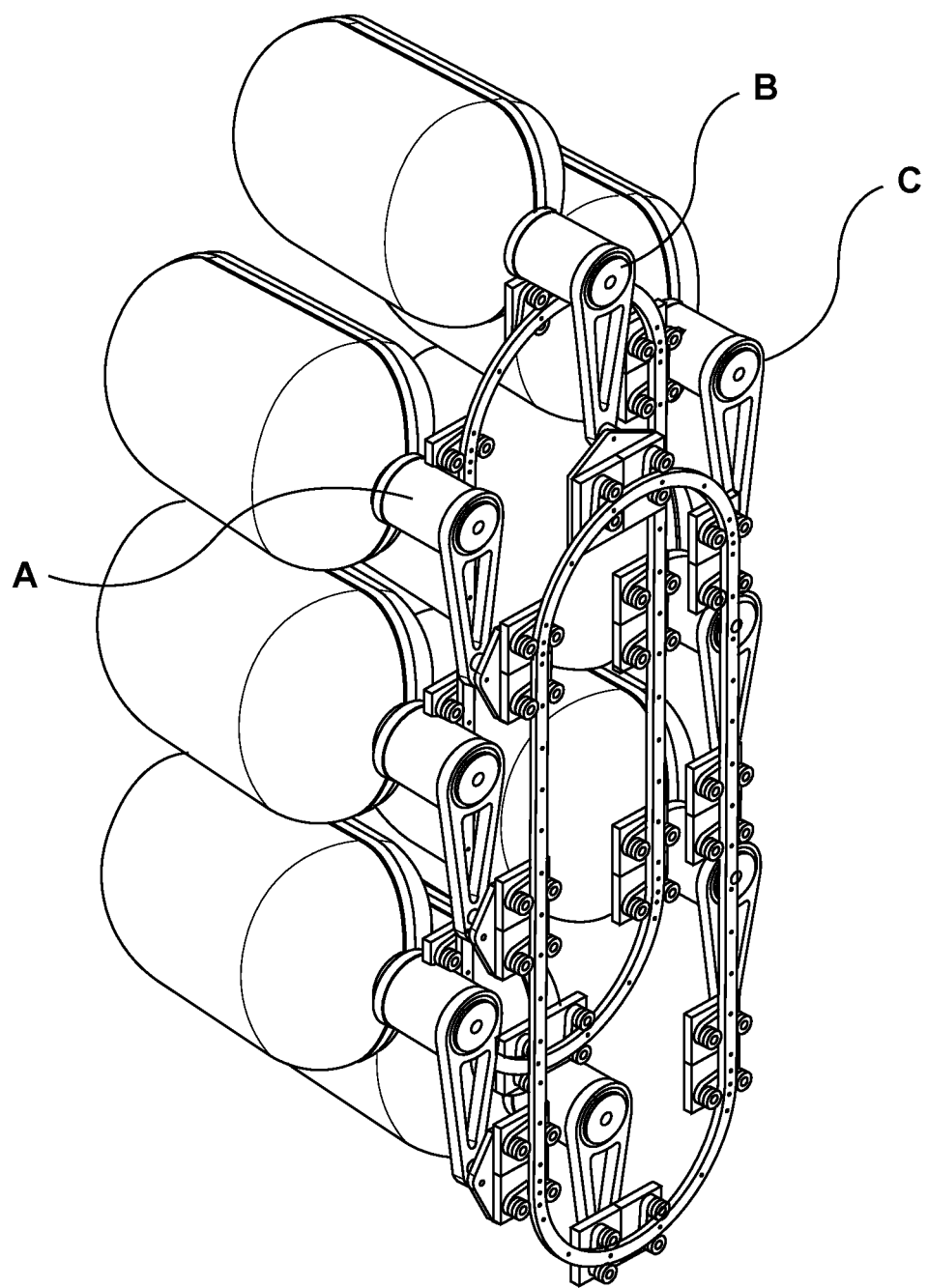
FIG. 7 shows front right side isometric perspective view of a carousel with a fully populated track assembly.

FIG. 7 shows a fully populated carousel illustrating the positioning of the translation assembly components with respect to the different positions of the biological production unit on the carousel both in the long runs and on the track bends. It is clear that regardless of the position of the biological production units along the tracks the resistance arm 40 is retained in its vertical position. During translational movement along the track bends, the outer hub shell 34 and the drive carriage 36 undergo rotational inversion while at the same time the support carriage pivots to undergo inversion. The drive carriages and the associated support carriages cooperatively move from position "A" (vertical), to position "B" (horizontal, as outer hub shell is undergoing rotational inversion), to position "C" (vertical inverted, rotational inversion is completed). Throughout this sequence, the resistance arm 40 is retained in a vertical orientation by virtue of the linkage mechanism.

In the production of patient-specific treatments, the necessity exists to enable independent operation of each biological production unit as the initialization, processing and completion of each patient specific production activity will not typically align with any other concurrent production requirements. Therefore, each biological production unit is independently controlled with respect to the biological processing conditions occurring therein. This necessitates the delivery of common resources to each biological production unit, where the consumption of such resources is controlled internally within each production unit.

The rotational movement of the plurality of biological production units presents a unique challenge for resource delivery and management. To minimize resource distribution complexity, a limit of about ±180 degrees rotation for the automated carousel is suitable. With this constraint on rotation, a robust and functionally reliable cabling strategy was developed for the conveyance of auxiliaries and resources (e.g. electrical power, supply gases and data).

Figure 8:
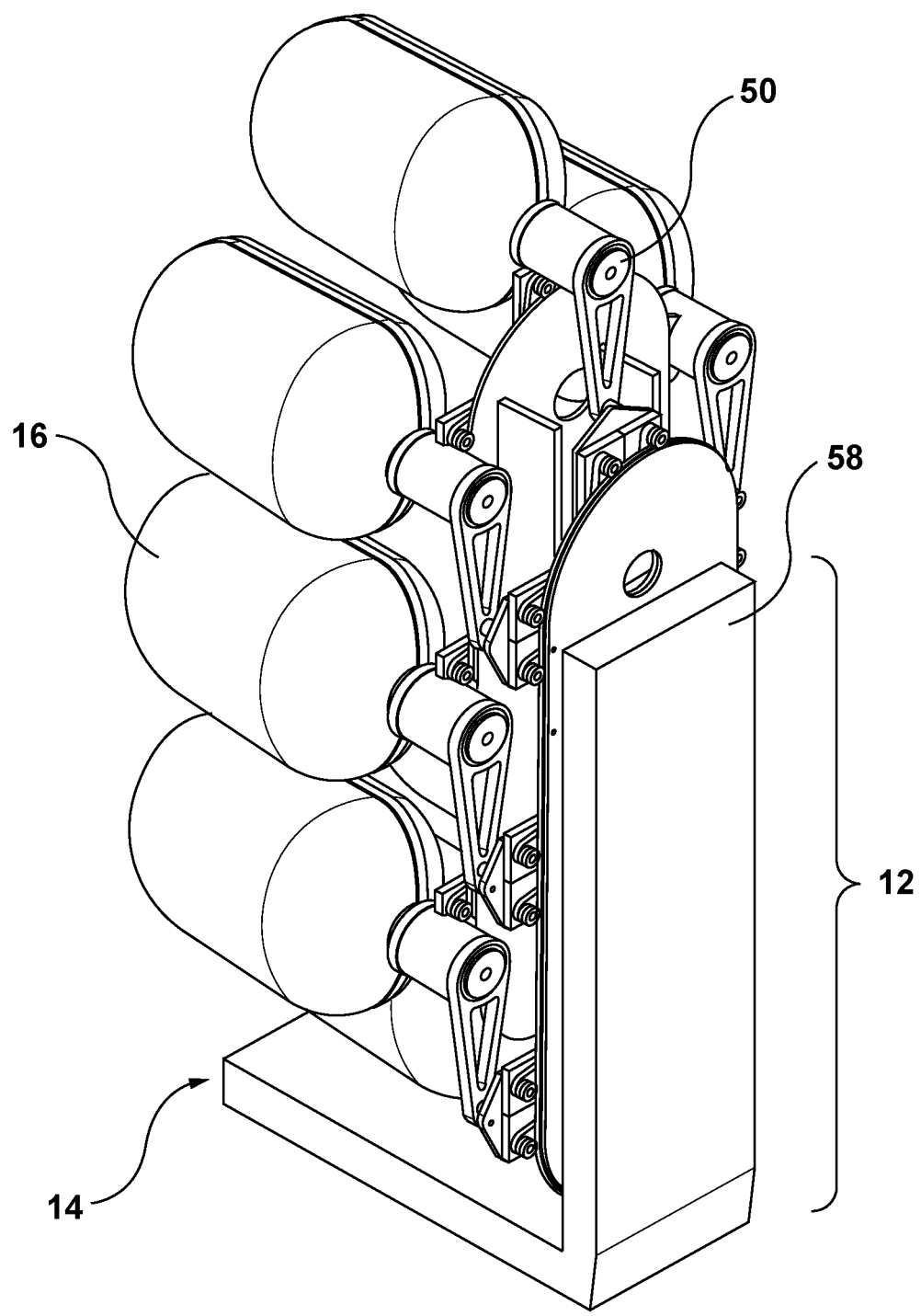
FIG. 8 is a front right side elevational view of the carousel system supported on a vertical housing having a support base.
Figure 9:
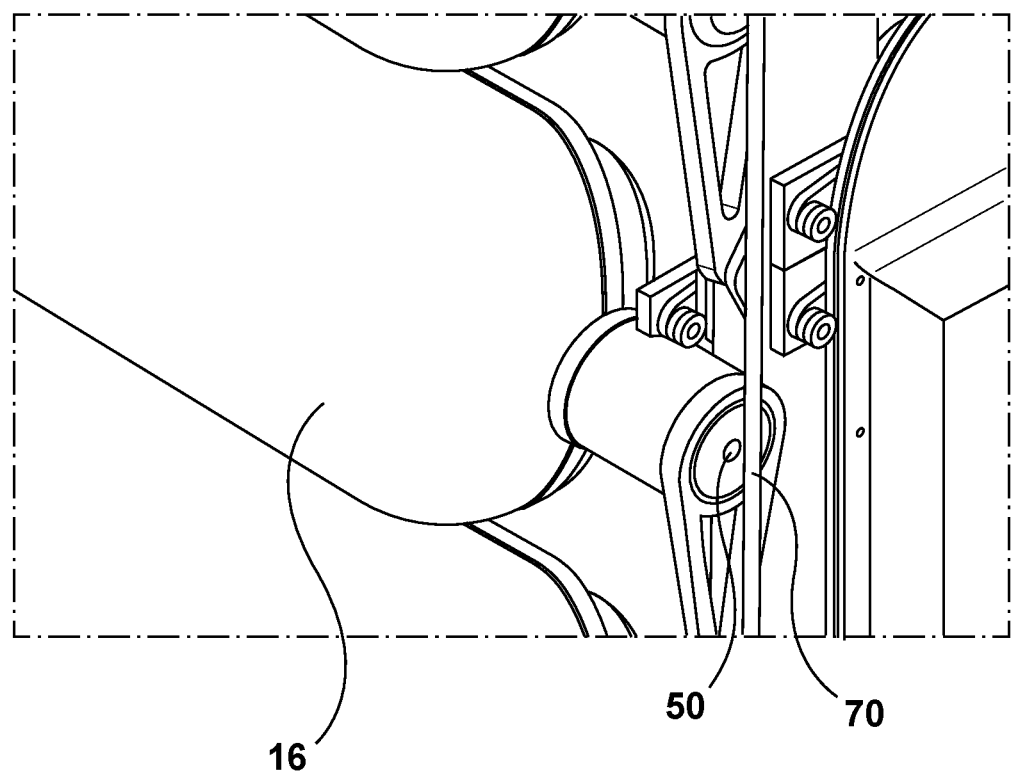
FIG. 9 shows a close up of the cabling used and connected with each of the biological production units that provides required resources from a central source.

FIG. 8 shows the complexity of a representative fully populated carousel operationally supported on the vertical housing assembly 12 supporting central operational resources for delivery. As shown in FIG. 9 each biological production unit is functionally attached via cabling (70) inserted via the port connection 50 that extends and is connected to the centrally located source within the vertical housing assembly 12. Cabling 70 from the central source is connected to a first biological production unit and onward to each successive biological production unit. This interlinked cabling strategy precludes the complexity of establishing independent cabling for resources for every biological production unit to the centrally located source.

Safety precautions are an operational requirement for the automated carousel in order to protect both the operator and the ongoing viability of the biological processes underway within each biological production unit. Moving parts are either contained or have an uninterrupted surface relative to other moving/stationary parts to prevent pinch points. In the event these conditions are not possible, alternate methods for avoiding injury are required. The housing assembly shown in FIG. 8 is configured with a protective cover 72 to further help to isolate and thus protect users from the resource distribution network and other parts.

A safety clutch is also provided to allow automatic interruption of movement of the carousel in the event higher than normal torque is encountered by the drive system of the automated carousel. The clutch slip at high torques protects the user from pinch hazards that can be created by the biological production units rotating along the track orbit and also avoids potentially damaging torques being transferred to other components within the automated carousel in the event of a malfunction.

Service and cleaning of the automated carousel is required for operation within GMP facilities. The temporary relocation of the automated carousel is potentially advantageous in maintaining a clean production space. Wheels 74 present underneath the base 14 are configured to deploy when portability is required. When stationary, the wheels 74 are retracted within the base to ensure stable placement of the base 14 relative to the underlying floor structure.

Figure 10:
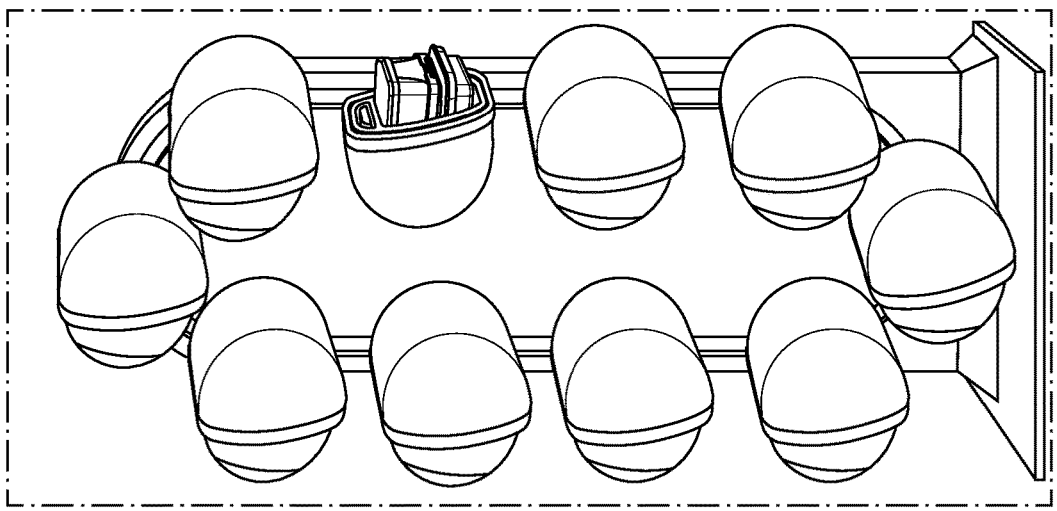
FIG. 10 shows three different sizes of the carousel that are shown to support, six, eight or ten biological production units.
Figure 10:
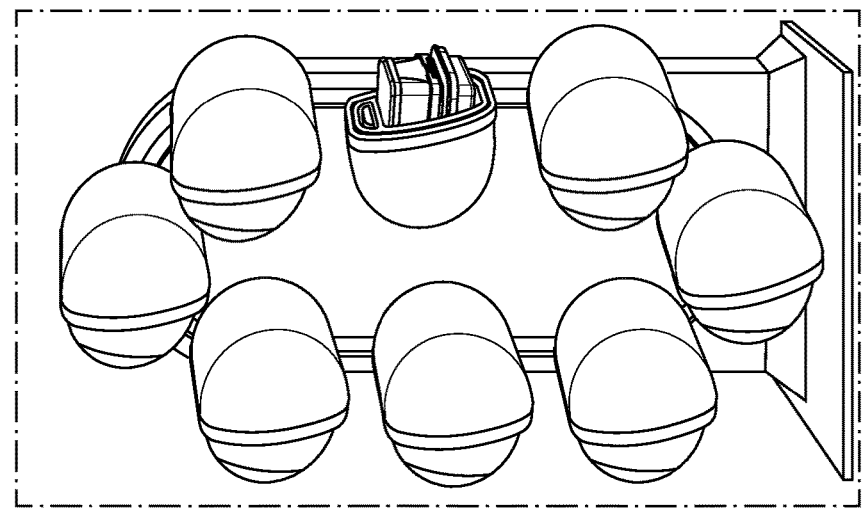
Figure 10:
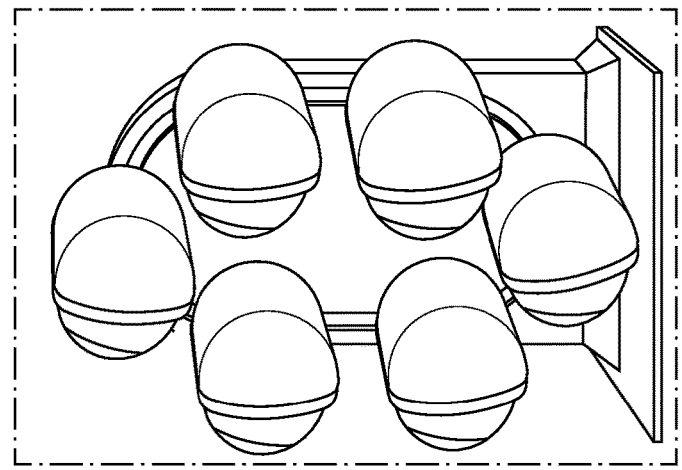

FIG. 10 shows representative configurations/sizes of the carousel supporting from 6 to 10 biological production units thereon. Fully populated "housed" carousels are also shown in series illustrating the much increased production capabilities of a biological facility for cell and/or tissue culture engineering. A carousel can be configured/sized to accommodate any number of biological production units. The height of the carousel is typically determined by the overhead clearance in the building in which it is to be installed. Generally, the carousel is constructed to have a maximum height compatible with the building structure to maximize the number of biological production units supported on a given carousel. For example, a carousel can be two or more stories in height, fitting within a two-three story (or more) building, to maximize the use of vertical space in the biological facility. In such embodiments, scaffolding and/or platforms can be added to the carousel to add structural integrity as well as to provide additional working areas for scientists to stand and monitor the biological production. The carousel can also span or physically incorporate walkways or platforms that allow technicians to access the carousel at different heights, and also allow for multiple access points to multiple users. Additional laboratory equipment can also be housed on the platforms as desired or needed to provide multiple working areas. A carousel can also be used to allow the movement of biological production units from one environmental class to another. For example, the carousel can span a sufficient height that a bottom section has a first cleanroom classification (e.g., a regulated cleanroom environment), then allow for translation of the biological production unit to an upper section that has a different clean room classification (e.g., an unregulated cleanroom environment, to allow for different production unit interactions to occur under different environmental conditions). Additional classifications can be envisioned as well.

The spacing between the biological production units is adjustable and is selected to provide adequate spacing for the size of the biological production unit. This allows customization of a given carousel for the particular type of biological production unit to be supported thereto. It should also be noted that although the figures illustrate all of the biological production units as being similar in type, it is within the scope of the present invention to simultaneously display various types of biological production units on a given carousel. It is further provided that the carousel and carousel systems may further be configured to have the separate ability to adjust the spacing of each biological unit relative to adjacent biological units so as to maximize the spatial density of biological units in selected zones of the carousel by close spacing and enhance user access to biological units in other selected zones by open spacing. In one non-limiting example, once a desired biological production unit is selected and properly positioned for a user, adjacent biological production units may be further translationally repositioned "away" from the selected biological production unit to provide more room for a user.

To accommodate different user access requirements, the biological production units may be precisely positioned for a selected user, by the user. An interface for the user to communicate effectively to each biological production unit on the carousel is provided and is adjustable.

Figure 11:
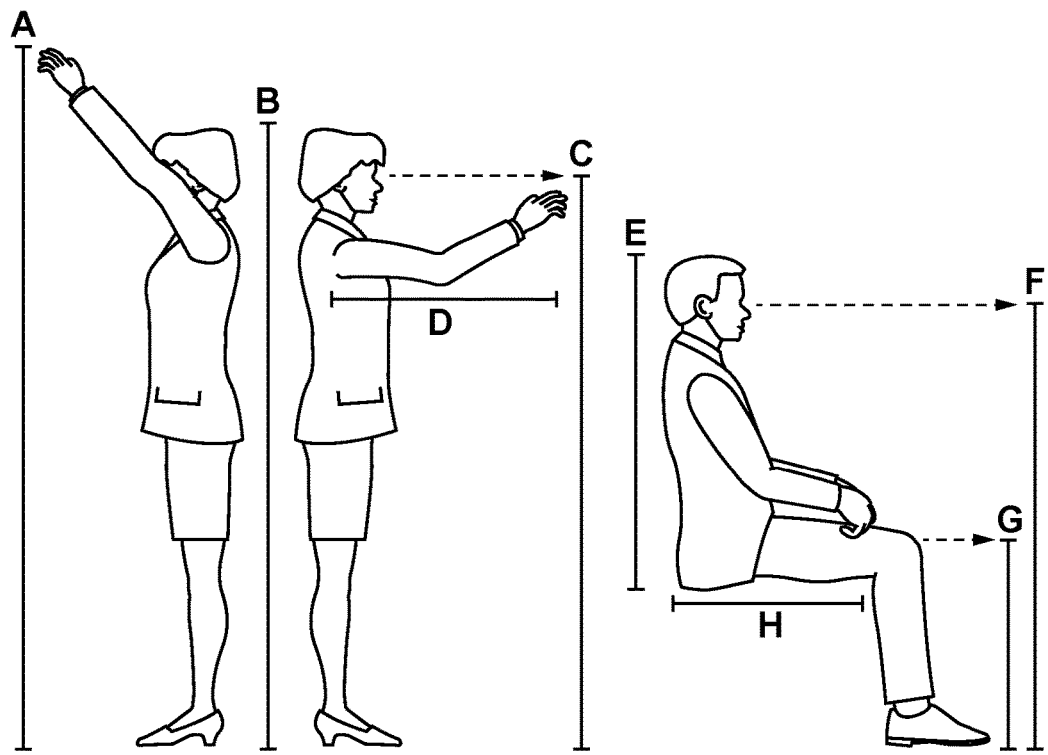
FIG. 11 shows representative measurements which can be used to define the range of placement of any specific biological production unit for ergonomic access by an operator.

FIG. 11 demonstrates representative measurements that can be used to define the range of placement of any specific production unit in order to provide ergonomic access by an operator. Thus using the automated carousel of the invention not only increases biological production, but provides a user easy and comfortable access to any one of the biological units either for inspection, for replacement, for removal or for repositioning. A user may place any of the biological production units at a vertical ergonomic level while standing or sitting.

As described herein, suitably the biological production units 16 are configured to move in unison or separately, so as to enable vertical positioning of any single unit for easy access. In embodiments, one or more additional stationary units can be mounted to the carousel as workflow units. These workflow units can be utilized for specific functions by removing a cassette from a unit currently translating in the carousel series, and transferring it to the stationary unit for additional processing. The stationary workflow units can also be utilized as a resource in the event temporary operational support is required to address a single biological production unit malfunction event. This temporary role can support unit repair or unit replacement.

In further embodiments, a secondary processing module can also be included in the carousels described herein. This secondary processing module can be engaged when a biological production unit 16 reaches a specific position in the translation. For example, the secondary processing module can be a bio-isolator to generate a controlled environment around a particular production unit for specific cassette handling requirements or other technical functions. This bio-isolator could allow an operator to intervene in the operation of a unit in ways not possible should the unit open into the general space (e.g., either external contamination, or a highly specialized or potentially toxic cell or virus being used in the units).

The foregoing illustrates the automated device of the invention achieves a further significant improvement to automated cell and tissue culture applications. Complex and automated modular biologic culture systems can be improved with the incorporation of the device of the invention allowing for a greater ability to provide much needed cells and tissues for patient treatment in the same space challenged facilities without compromise of the integrity of the system, or the versatility of the system. Operation of each biological production unit in terms of access at any time is ergonomic and easily achievable by any user as desired.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. It is, therefore, to be understood that the foregoing embodiments are presented by way of example only and that, within the scope of the appended claims and equivalents thereto, the invention may be practiced otherwise than as specifically described and claimed.

The descriptions of the various embodiments and/or examples of the present invention have been presented for purposes of illustration but are not intended to be exhaustive or limited to the embodiments and/or examples disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. An automated carousel comprising:
a substantially vertical track assembly comprising an upright drive track and a support track;
a plurality of translation assemblies, wherein each of the plurality of translation assemblies is a hub assembly having a first end defining a coupling for an input shaft of a biological production unit in a cantilevered orientation, and
a central hub comprising:
an inner hub configured to axially rotate the biological production unit; and
a resistance arm having a pivotally connected support carriage cooperatively engaged with the support track for translational movement thereon;
wherein each translation assembly supports a biological production unit in a cantilevered orientation, said plurality of translation assemblies configured to provide: (i) separate translational movement of each biological production unit along the drive track and the support track, while maintaining the cantilevered orientation of each biological production unit stable with respect to gravity, and separately, (ii) axial rotation of each biological production unit.

2. The automated carousel of claim 1, wherein the central hub further includes an outer hub shell supporting a drive carriage for cooperatively engaging with the drive track for translational movement thereon.

3. The automated carousel of claim 1, wherein the inner hub comprises a motor driven central shaft for engaging with the input shaft of the biological production unit, wherein actuation of the motor actively rotates the central shaft at a controlled speed causing axial rotation of the associated biological production unit.

4. The automated carousel of claim 2, wherein the drive carriage comprises a drive block assembly with one face thereof comprising affixed vertically arranged pairs of outwardly projecting bearing members for gripping the drive track and for engaging with a drive belt or a drive linkage adapted to move along the course of travel defined by the drive track.

5. The automated carousel of claim 1, wherein the support carriage comprises a support block assembly with one face thereof comprising affixed vertically arranged pairs of outwardly projecting bearing members for gripping the support track and for engaging with a drive belt or a drive linkage adapted to move along the course of travel defined by the support track.

6. The automated carousel of claim 1, wherein a second end of the hub assembly comprises a port for entry of a connector for centrally provided operational resources to the biological production unit.

7. The automated carousel of claim 6, wherein said port leads to a hollow shaft extending through the central hub to the biological production unit.

8. The automated carousel of claim 7, wherein the connector comprises cabling enclosing separate operational resources, the cabling originating from a central source and connecting each successive biological production unit on said carousel.

9. The automated carousel of claim 8, wherein the operational resources are electrical supply lines, gas supply lines and controller connections.

10. The automated carousel of claim 1, wherein said biological production unit is a cell and/or tissue engineering system configured to perform one or more of: sterile reception/storage of tissue biopsy; automated monitoring of digestion process; digestion of biopsy tissue to yield disassociated cells; cell sorting and selection; safe waste collection; cell seeding on or within a proliferation substrate; scaffold proliferation of cells to expand cell populations; cell washing and cell collection; cell seeding on or within a tissue engineering scaffold or matrix; cell differentiation to allow specialization of cellular activity; tissue formation; mechanical and/or biochemical stimulation to promote tissue maturity; harvest of tissue engineered constructs/implants for reconstructive surgery; and storage and transportation of cells and implantable tissue.

11. The automated carousel of claim 1, wherein the translational movement of each biological production unit along the drive track and support track, and separately, the axial rotation of each biological production unit, allow for ergonomic access to each biological production unit by a user.

12. An automated carousel system for the distribution and ergonomic positioning of multiple biological production units, each of the biological production units comprising an automated individually operable cell and/or tissue engineering system, the automated carousel system comprising:
an automated carousel comprising:
a substantially vertical track assembly comprising a drive track and a support track vertically offset and spaced apart from one another; and
a plurality of translation assemblies connecting the drive track and the support track at spaced apart positions, wherein each of the plurality of translation assemblies is a hub assembly having a first end defining a coupling for an input shaft of the biological production unit in a cantilevered orientation, and a second end having a vertically downward extending resistance arm, and
a central hub comprising:
an inner hub comprising a central shaft for engaging with the input shaft of the biological production unit, the central shaft mounted to the vertically downward extending resistance arm of the second end, the inner hub configured to axially rotate the biological production unit; and
the vertically downward extending resistance arm having a pivotally connected support carriage cooperatively engaged with the support track for translational movement thereon;
each of said plurality of translation assemblies supporting each biological production unit in the cantilevered orientation, wherein said plurality of translation assemblies are configured to provide: (i) separate translational movement of each biological production unit along the connected drive track and support track while maintaining the cantilevered orientation of each biological production unit stable with respect to gravity, and separately, (ii) axial rotation of each biological production unit;
a controller for independent biological control of each cell and/or tissue engineering system within each of said biological production units;
a vertical housing assembly supporting the automated carousel, the housing assembly comprising a central source of operational resources;
a connector for interconnecting the central source of operational resources to each successive biological production unit; and
a computer connection.

13. The automated carousel system of claim 12, wherein each biological production unit comprises a connected interface for communication by a user, said connected interface connected to the computer connection.

14. The automated carousel system of claim 12, comprising up to 24 translation assemblies.

15. The automated carousel system of claim 12, wherein the translational movement of each biological production unit along the connected drive track and support track, and separately, the axial rotation of each biological production unit, allow for ergonomic access to each biological production unit by a user.

* * * * *